United States Patent
Johnston

(10) Patent No.: US 8,017,348 B1
(45) Date of Patent: *Sep. 13, 2011

(54) ASSAY FOR PARKINSON'S DISEASE THERAPEUTICS

(75) Inventor: Jennifer A. Johnston, Mill Valley, CA (US)

(73) Assignee: Elan Pharma International Limited, Monksland, Athlone, County Westmeath (IE)

(*) Notice: Subject to any disclaimer, the term of this patent is extended or adjusted under 35 U.S.C. 154(b) by 226 days.

This patent is subject to a terminal disclaimer.

(21) Appl. No.: 12/177,100

(22) Filed: Jul. 21, 2008

Related U.S. Application Data

(63) Continuation-in-part of application No. 11/638,242, filed on Dec. 12, 2006.

(60) Provisional application No. 60/950,857, filed on Jul. 19, 2007, provisional application No. 60/749,964, filed on Dec. 12, 2005.

(51) Int. Cl.
| | |
|---|---|
| G01N 33/567 | (2006.01) |
| G01N 33/53 | (2006.01) |
| C12Q 1/68 | (2006.01) |
| C12N 1/21 | (2006.01) |
| C12N 15/85 | (2006.01) |
| C12N 15/00 | (2006.01) |
| C40B 30/00 | (2006.01) |

(52) U.S. Cl. ......... 435/7.21; 435/7.1; 435/6; 435/252.3; 435/325; 435/320.1; 506/7

(58) Field of Classification Search .................. None
See application file for complete search history.

(56) References Cited

U.S. PATENT DOCUMENTS

| | | | |
|---|---|---|---|
| 4,758,571 A | 7/1988 | Curtius et al. | |
| 2004/0214763 A1 | 10/2004 | Corti et al. | |
| 2005/0042607 A1* | 2/2005 | Mizuno et al. | 435/6 |
| 2006/0159681 A1 | 7/2006 | Lozano et al. | |

FOREIGN PATENT DOCUMENTS

| | | |
|---|---|---|
| EP | 1 416 272 A1 | 5/2004 |
| WO | WO 02/079459 A2 | 10/2002 |
| WO | WO 2007/089334 A2 | 8/2007 |
| WO | WO 2007/089334 A3 | 8/2007 |

OTHER PUBLICATIONS

Harvard Medical School Protocol, pp. 1-12, 2002.*
Dawson et al (Nature Neurosc supp 5: 1058-1061, 2002).*
U.S. Appl. No. 12/096,890, filed Jun. 10, 2008, Johnston.
U.S. Appl. No. 60/950,857, filed Jul. 19, 2007, Johnston.
U.S. Appl. No. 11/638,242, filed Dec. 12, 2006, Johnston.
U.S. Appl. No. 60/749,964, filed Dec. 12, 2005, Johnston.
U.S. Appl. No. 60/750,009, filed Dec. 12, 2005, Johnston.
Bandopadhyay et al., "Synphilin-1 and parkin show overlapping expression patterns in human brain and form aggresomes in response to proteasomal inhibition," *Neurobiology of Disease*, 20: 401-411 (2005).
Bence et al., "Impairment of the Ubiquitin-Proteasome System by Protein Aggregation," *Science*, 292: 1552-1556 (2001).
Cookson, M.R., "Molecules that Cause or Prevent Parkinson's Disease," *PLoS Biol.*, 2(11): 1717-1720 e401 (2004).
Finney et al., "The Cellular Protein Level of Parkin is Regulated by Its Ubiquitin-like Domain," *J. Biol. Chem.*, 278(18):16054-16058 (2003).
Gu et al., "The C289G and C418R Missense Mutations Cause Rapid Sequestration of Human Parkin into Insoluble Aggregates," *Neurobiology of Disease*, 14:357-364 (2003).
Hammarstrom et al., "Prevention of Transthyretin Amyloid Disease by Changing Protein Misfolding Energetics," *Science*, 299: 713-716 (2003).
Hyun et al., Effect of Wild-type of Mutant Parkin on Oxidative Damage, Nitric Oxide, Antioxidant Defenses, and the Proteasome, *The Journal of Biological Chemistry*, 277(32):28572-28577 (2002).
Hyun et al., "Effect of Overexpression of Wild-type or Mutant Parkin on the Cellular Response Induced by Toxic Insults," *Journal of Neuroscience Research*, 82:232-244 (2005).
Junn et al., "Parkin Accumulation in Aggresomes Due to Proteasome Impairment," *J. Biol. Chem.*, 277(49): 47870-47877 (2002).
Kuroda et al., "Parkin enhances mitochondrial biogenesis in proliferating cells", Human Molecular Genetics, 15(6):883-895 (2006).
Luo et al., "Are Heat Shock Proteins Therapeutic Target for Parkinson's Disease?," Internation of Journal of Biological Scienses, 3(1):20-26 (2007).
Matsuda et al., "Diverse Effects of Pathogenic Mutations of Parkin that Catalyze Multiple Monoubiquitylation in Vitro", Journal of Biological Chemistry, 281(6):3204-3209, (2005).
Millard et al., "Stabilization of a metastable state of *Torpedo californica* acetylcholinesterase by chemical chaperones," *Protein Science*, 12:2337-2347 (2003).
Muqit et al., "Parkin is recruited into aggresomes in a stress-specific manner: over-expression of parkin reduces aggresome formation but can be dissociated from parkin's effect on neuronal survival," *Human Molecular Genetics*, 13(1):117-135 (2004).
Perlmutter, D.H., "Chemical Chaperones: A Pharmacological Strategy for Disorders of Protein Folding and Trafficking," *Pediatric Research*, 52:832-836 (2002).
PCT International Search Report of Nov. 20, 2007 for application PCT/US2006/047515.
PCT International Preliminary Examination Report on Patentability of Mar. 11, 2008 for application PCT/US2006/047515.

(Continued)

*Primary Examiner* — Ali R. Salimi
*Assistant Examiner* — Aditi Dutt
(74) *Attorney, Agent, or Firm* — Alston & Bird LLP

(57) ABSTRACT

The invention provides to assays for agent useful for treatment of Parkinson's Disease. Included are cell-based assays for agents that modulate the effect of Parkin proteins on proteasome function.

20 Claims, 11 Drawing Sheets

OTHER PUBLICATIONS

PCT Written Opinion of Nov. 20, 2007 for application PCT/US2006/047515.

Rankin et al., "E3 Ubiquitin-Protein Ligase Activity of Parkin Is Dependent on Cooperative Interaction of RING Finger (TRIAD) Elements," *J. Biomed. Sci.*, 8:421-429 (2001).

Sawkar et al., "Chemical chaperones increase the cellular activity of N3705 β-glucosidase: A therapeutic strategy for Gaucher disease," *PNAS*, 99(24):15428-15433 (2002).

Shang et al., Sepiapterin Attenuates 1-methyl-4-phenylpyridinium-induced Apoptosis in Neuroblastoma Cells Transfected with Neuronal NOS: Role of Tetrahydrobiopeterin, Nitric Oxide, and Proteasome Activation, *Free Radical Biology & Medicine*, 39:1059-1074 (2005).

Tanaka et al., "Parkin is linked to the ubiquitin pathway," *J. Mol. Med.*, 79:482-494 (2001).

Trzesniewska et al., "Neurodegenerative aspects of protein aggregation," *Acta Nurobiol Exp*, 64:41-52 (2004).

U.S. Appl. No. 11/638,242, Office Action mailed Jan. 27, 2009.
U.S. Appl. No. 11/638,242, Office Action mailed Apr. 18, 2008.
U.S. Appl. No. 11/638,242, Office Action mailed Aug. 23, 2007.

Wang et al., "Alterations in the solubility and intracellular localization of parkin by several familial Parkinson's disease-linked point mutations," *J. Neurochem.*, 93:422-431 (2005).

Yam et al., "A synthetic chaperone corrects the trafficking defect and disease phenotype in a protein misfolding disorder," *FASEB J.*, 19:12-18 (2005).

Sawkar et al., "Chemical chaperones and Permissive Temperatures Alter the Cellular Localization of Gaucher Disease Associated Glucocerebrosidase Variants," *ACS Chemical Biology*, 1(4):235-251 (2006).

U.S. Appl. No. 11/638,242, Examiner Interview Summary mailed Apr. 28, 2009.

* cited by examiner

FIGURE 1
FIG. 1A
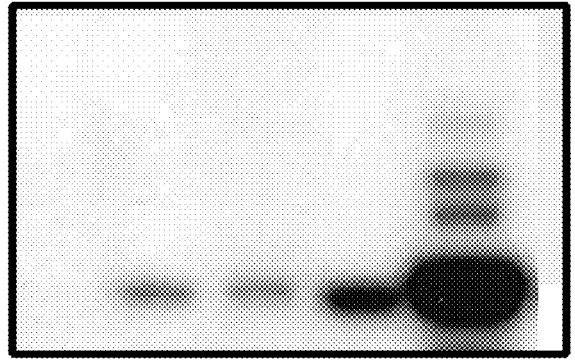
FIG. 1B

FIGURE 2
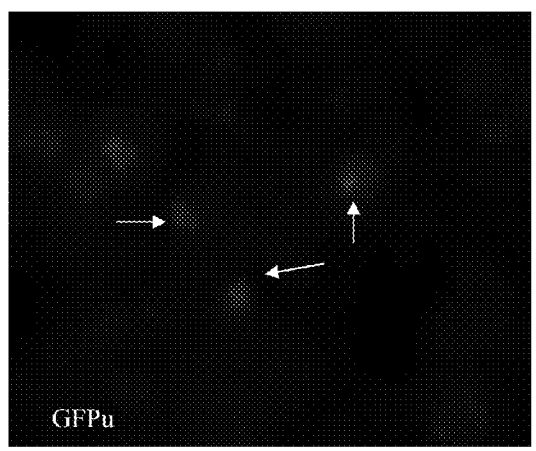
FIG. 2A
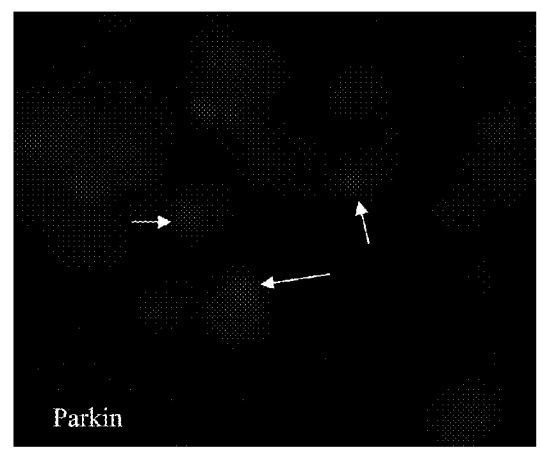
FIG. 2B
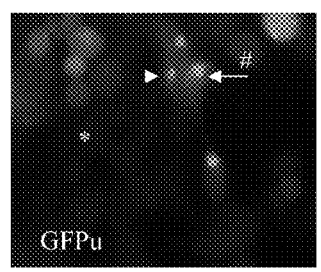
FIG. 2C
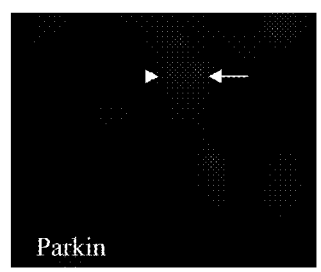
FIG. 2D
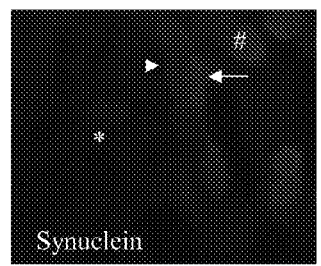
FIG. 2E FIGURE 7
FIG. 7A
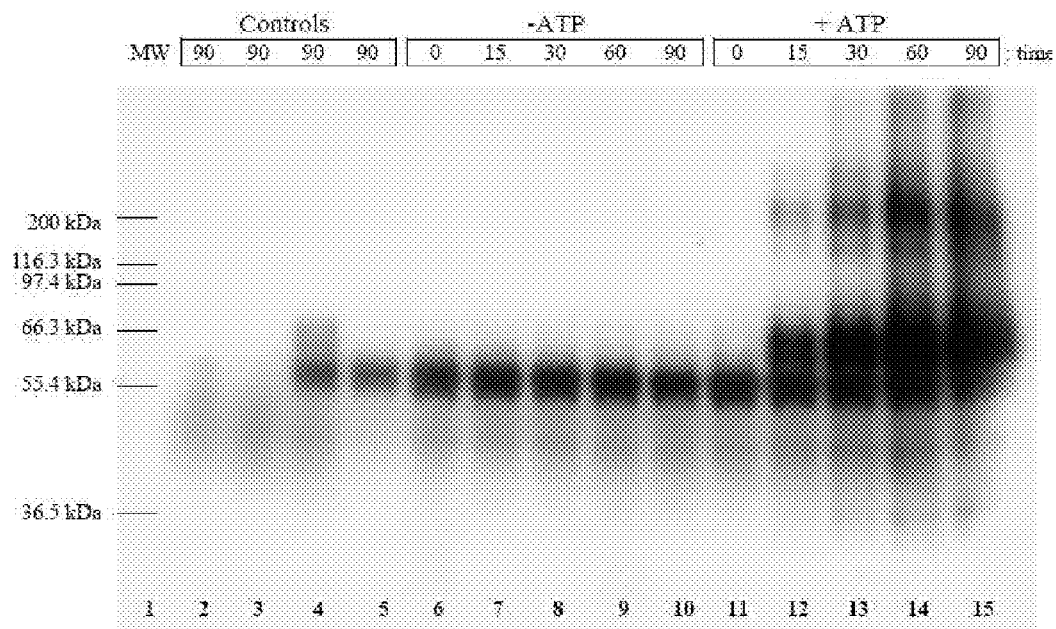
FIG. 7B
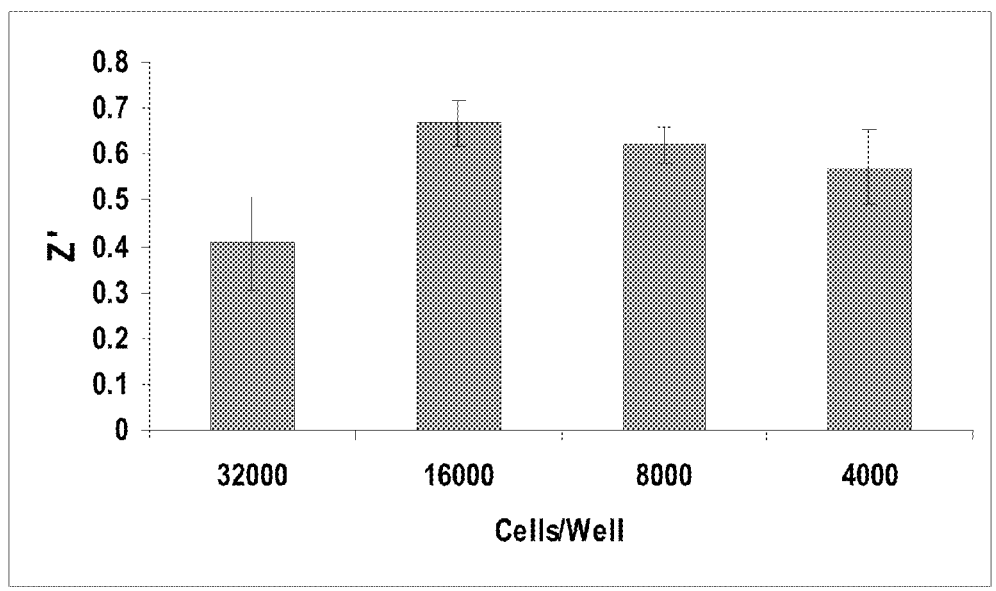

Figure 8. Effect of DMSO on Assay Performance
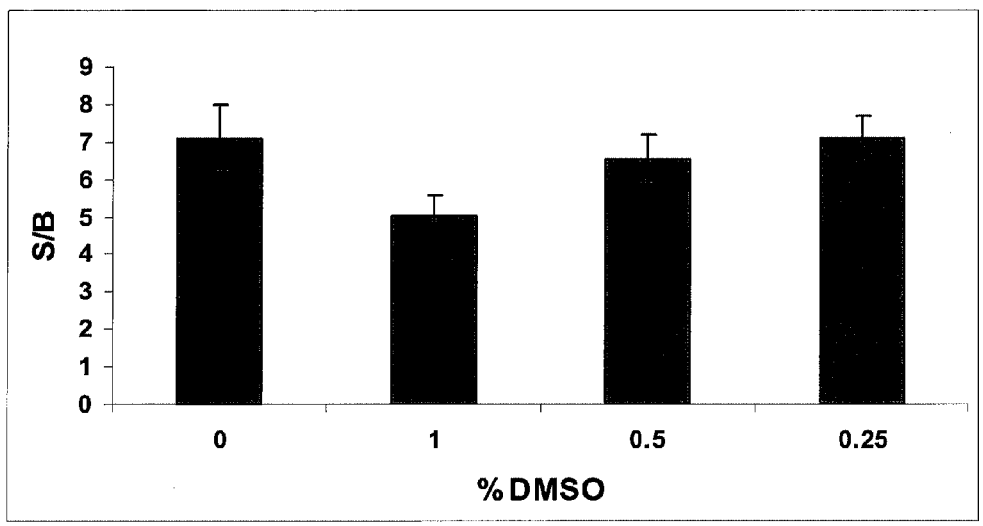
Figure 9. Increasing DNA Transfection Concentrations Does Not Result in Increased Signal/Backgrounds
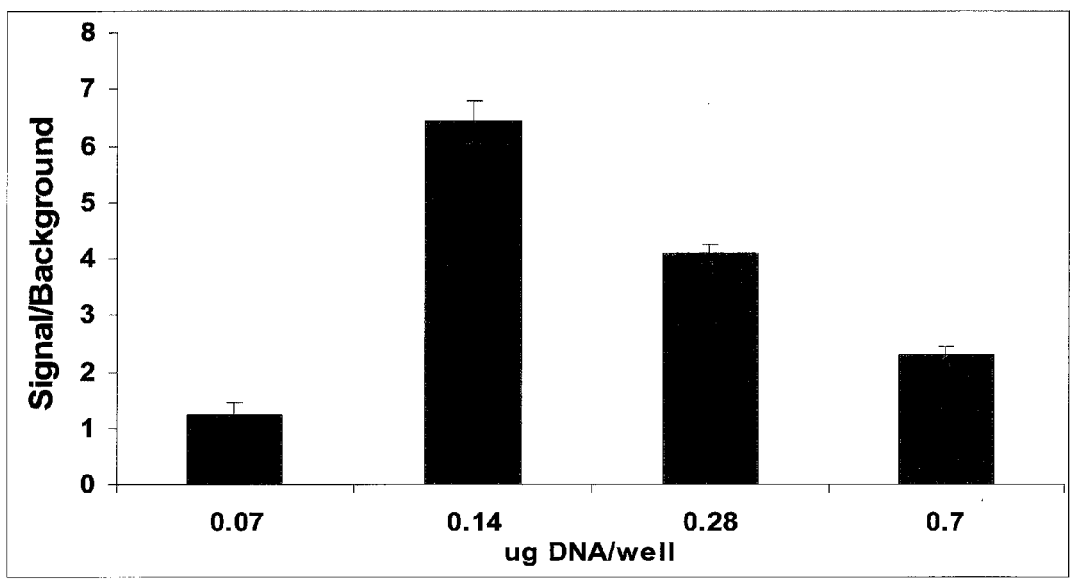

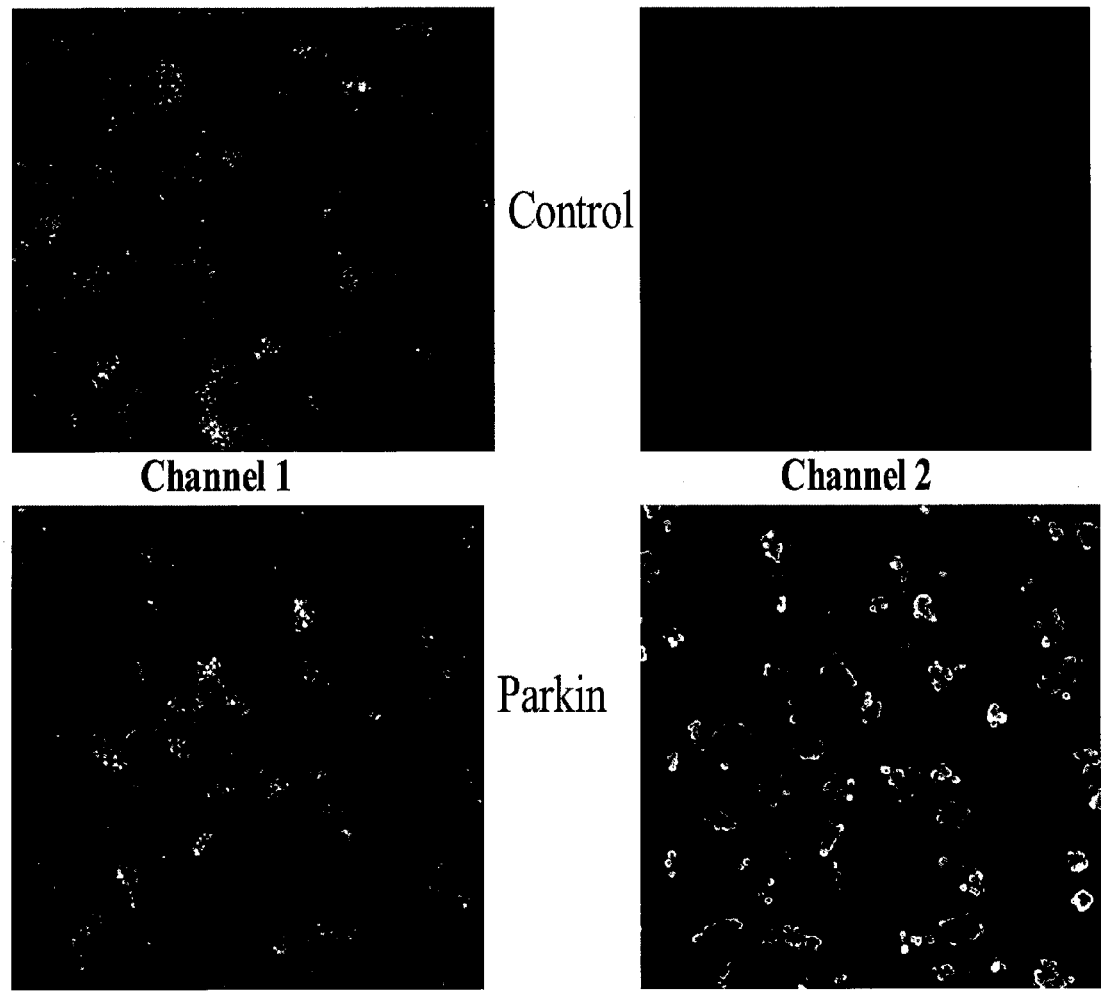
Figure 10. Parkin Antibody Staining of HEK293 Transfected Cells Indicates > 60% Transfection Efficiency.

Figure 11. Time Course For Development of Signal in the GFPu Assay.
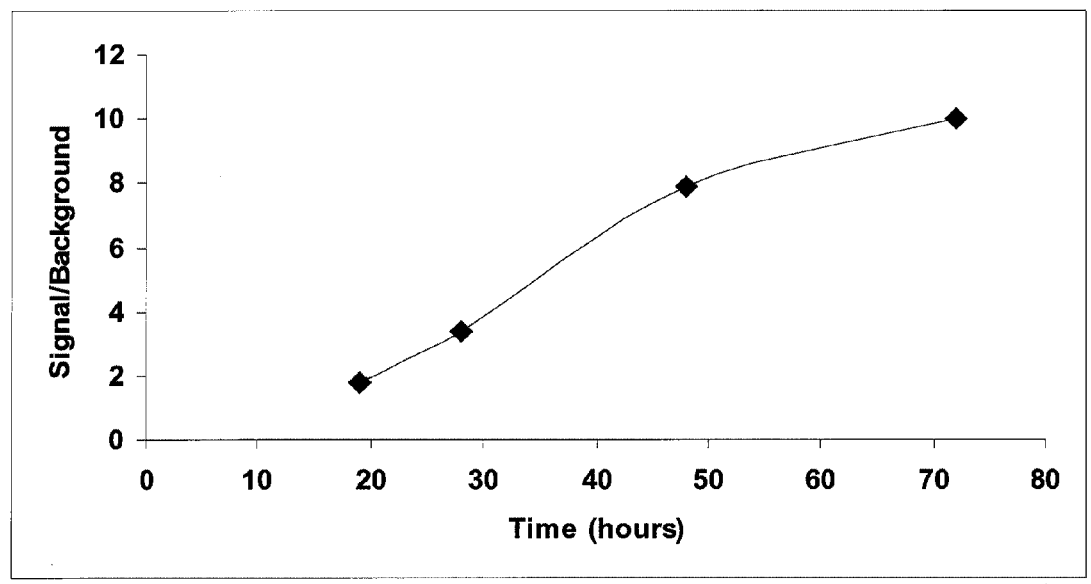

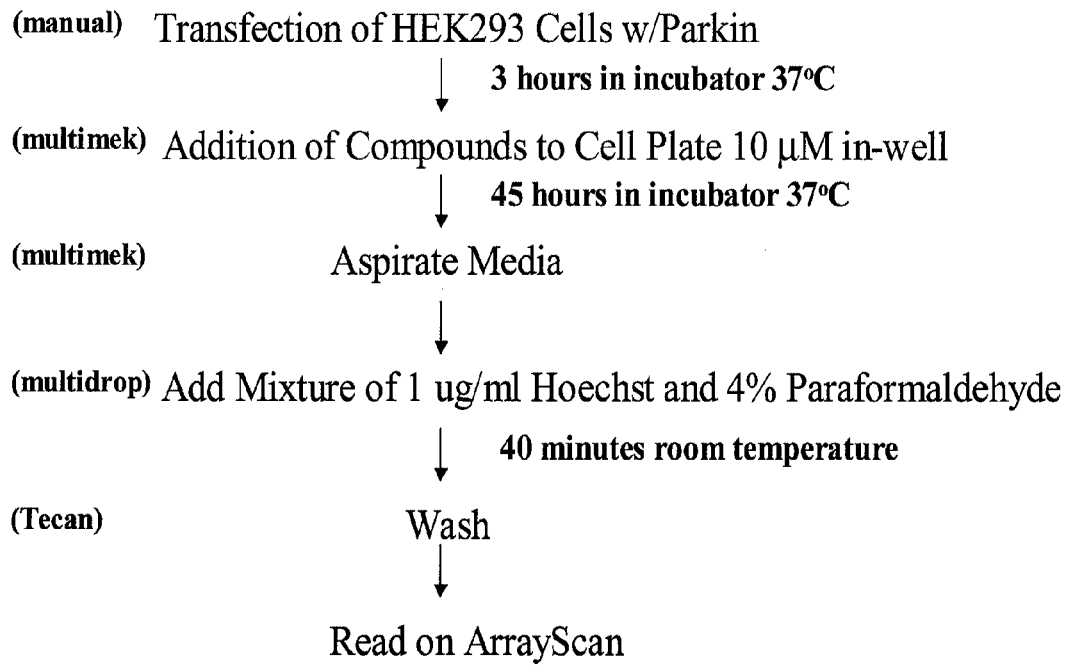
Figure 12. Automation Scheme For the GFPu Assay

ASSAY FOR PARKINSON'S DISEASE THERAPEUTICS

CROSS-REFERENCE TO RELATED APPLICATIONS

The application is a continuation-in-part of copending U.S. application Ser. No. 11/638,242, filed Dec. 12, 2006 and claims benefit of U.S. provisional application No. 60/950,857, filed Jul. 19, 2007. The entire disclosures of these applications are incorporated herein by reference.

FIELD OF THE INVENTION

The invention relates to assays for agent useful for treatment of Parkinson's Disease. The invention finds application in the fields of drug discovery and medicine.

BACKGROUND

Parkinson's disease (PD) is a neurological disorder characterized neuropathologically as a loss of dopamine neurons of the substantia nigra. This neuronal loss manifests clinically as alterations in movement, such as Bradykinesia, rigidity and/or tremor (Gelb et al., 1999, *Arch. Neurol.* 56: 33-39). Analysis of human genetic data has been used to characterize genes linked to the development of PD. One of these genes was localized to chromosome 6 using a cohort of juvenile onset patients and identified specifically as Parkin protein (Kitada et al., 1998, *Nature* 392: 605-608). Parkin protein has been shown to be an E3 ligase protein that functions in the ubiquitin-proteasome system (UPS) (Shimura, 2000, *Nature Genetics* 25:302-305). The UPS is a major cellular pathway involved in the targeted removal of proteins for degradation and E3 ligases function to identify and label substrates for degradation by cellular proteasomes (Hereshko and Cienchanover, 1998, *Ann. Rev. Biochem.* 67; 425-479) or lysosomes (Hicke, 1999, *Trends in Cell Biology* 9:107-112).

There is an urgent need for new methods for treating Parkinson's disease. The present invention provides methods and materials that are useful for identifying and/or validating agents for PD therapy, as well as for other uses.

BRIEF SUMMARY OF THE INVENTION

In one aspect, the invention provides assays for identification of, or screening for, compounds useful for treatment of Parkinson's Disease (PD). In one aspect, the invention provides a cell-based assay for identifying a candidate compound for treatment of Parkinson's Disease including (a) exposing a mammalian cell expressing Parkin to a test agent; and (b) comparing proteasome function in the cell with proteasome function characteristic of a corresponding mammalian cell expressing Parkin not exposed to the test compound; where an increased level of proteasome function in the cell exposed to the test agent indicates the agent is a candidate compound for treatment of Parkinson's Disease.

In a related aspect the invention provides a cell-based assay for identifying a candidate compound for treatment of Parkinson's Disease including (a) obtaining mammalian cells expressing Parkin; (b) exposing a cell to a test agent; and (c) comparing proteasome function in the cell with proteasome function in a cell not exposed to the test agent; where an increased level of proteasome function in the cell exposed to the test agent indicates the agent is a candidate compound for treatment of Parkinson's Disease.

Various methods may be used to measure or assess proteasome function. In one embodiment, the mammalian cells express GFPu and proteasome function is measured by measuring the amount of GFPu in the cells. In one embodiment the amount of GFPu in the cells is determined by measuring GFPu fluorescence.

In some cases the cell-based screening method also includes a proteasome function assay including (i) exposing a mammalian cell expressing a mutant Parkin to the candidate compound; and (ii) comparing proteasome function in the cell in with proteasome function characteristic of a cell expressing a mutant Parkin not exposed to the candidate compound.

In some cases the cell-based screening method also includes a proteasome function assay including (i) exposing a mammalian cell expressing another protein, such as Huntingtin, to the candidate compound; and (ii) comparing proteasome function in the cell with proteasome function characteristic of a cell expressing the other protein and not exposed to the candidate compound.

In some cases the cell-based screening method also includes an in vitro activity assay including (i) measuring the autoubiquitination activity of a purified Parkin protein in the presence of the compound; and (ii) comparing the autoubiquitination activity of purified Parkin protein in the presence of the compound with autoubiquitination activity of purified Parkin protein in the absence of the compound.

In some cases the cell-based screening method also includes an in vitro activity binding assay including (i) contacting the compound with purified Parkin protein and (ii) detecting the binding, if any, of the compound and the Parkin protein.

The invention provides a method for identifying a candidate compound for treatment of Parkinson's Disease comprising (a) exposing a mammalian cell expressing exogenous Parkin to a test agent; (b) comparing proteasome function in the cell and proteasome function characteristic of a corresponding mammalian cell expressing Parkin but not exposed to the test agent; wherein an increased level of proteasome function in the cell exposed to the test agent indicates the agent is a candidate compound for treatment of Parkinson's Disease. In some cases the cell in (a) does not express an exogenous mammalian protein other than Parkin. In some cases, the Parkin in (a) is a Parkin mutant for which heterozygosity is correlated to development of PD.

In some embodiments the cells in (a) are cells transiently transfected with an expression vector encoding Parkin. In certain embodiments of the method, after transfection is initiated the cells are incubated 2-5 hours prior to addition of the test agent. In certain embodiments proteasome function is measured about 45 hours after addition of the test agent. In certain embodiments the cells are plated at a density of about 250-500 cells per $mm^2$. For example, 8,000-16,000 cells per well may be plated in wells having a surface area of about 32.15 $mm^2$.

In one aspect further assays are carried out to identify or validate agents as candidate compounds for treatment of PD. In one approach the method further includes a selectivity assay comprising (i) exposing a mammalian cell expressing an exogenous mammalian protein other than Parkin to the test agent or candidate compound; (ii) comparing proteasome function in the cell in (i) and proteasome function characteristic of a cell expressing the exogenous mammalian protein but not exposed to the test agent or candidate compound; and (iii) identifying agents or compounds that increase proteasome function in cells expressing Parkin, but not in cells expressing said exogenous mammalian protein other than Parkin. In some embodiments the exogenous mammalian protein is Huntingtin, NRDP1, SOD1, Rhodopsin, connexin 43, $Ub^{+1}$, presenilin, or Cystic Fibrosis Transmembrane Conductance Regulator (CFTR).

In one approach the method further includes an in vitro activity assay comprising (i) measuring the E3 ligase activity of Parkin protein in the presence of the test agent or candidate compound; and (ii) comparing the E3 ligase activity of Parkin protein in the presence of the test agent or candidate compound with E3 activity of Parkin protein in the absence of the agent or compound. The E3 ligase activity of purified Parkin protein or Parkin expressed in cells may be assayed.

In one approach the method further includes an in vitro binding assay comprising (i) contacting the test agent or candidate compound with purified Parkin protein; and, (ii) detecting the binding, if any, between the agent or compound and the Parkin protein.

In one aspect the invention provides a high-throughput screening method comprising assaying at least 25 test agents in parallel using the methods described herein. In one embodiment the assay is carried out in 96-well cell culture plates. In one embodiment the method involves (a) exposing a plurality of aliquots of mammalian cells expressing exogenous Parkin to test agents; and (b) comparing proteasome function of cells in each aliquot with proteasome function characteristic of corresponding mammalian cells expressing Parkin but not exposed to any of said test agents; wherein an increased level of proteasome function in cells exposed to a test agent compared to cells not exposed to any test agent indicates the test agent is a candidate compound for treatment of Parkinson's Disease. In one embodiment the aliquots of mammalian cells expressing exogenous Parkin are transfected with a Parkin-encoding polynucleotide 2-4 hours prior to exposure to test agents and proteasome function is measured in the cells after 40-50 hours of exposure to the test agents.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A and 1B show immunoblots demonstrating that overexpression of Parkin results in impaired proteasome activity.

FIGS. 2A-E shows epifluorescent and immunofluorscent images illustrating that expression of Parkin protein leads to stabilization and aggregation of other proteasome substrates such as GFPu.

FIGS. 7A and 7B show the effect of Cell Density on Assay Quality.

FIG. 8 shows the effect of DMSO on Assay Performance.

FIG. 9 shows that increasing DNA transfection concentrations does not result in increased signal/backgrounds.

FIG. 10 shows Parkin antibody staining of HEK293 cells transfected with a Parkin expression vector, establishing greater than 60% transfection efficiency.

FIG. 11 is a time course for development of signal in the GFPu assay.

FIG. 12 shows an automation scheme for the GFPu Assay.

DETAILED DESCRIPTION

I. Introduction

Figure 3:
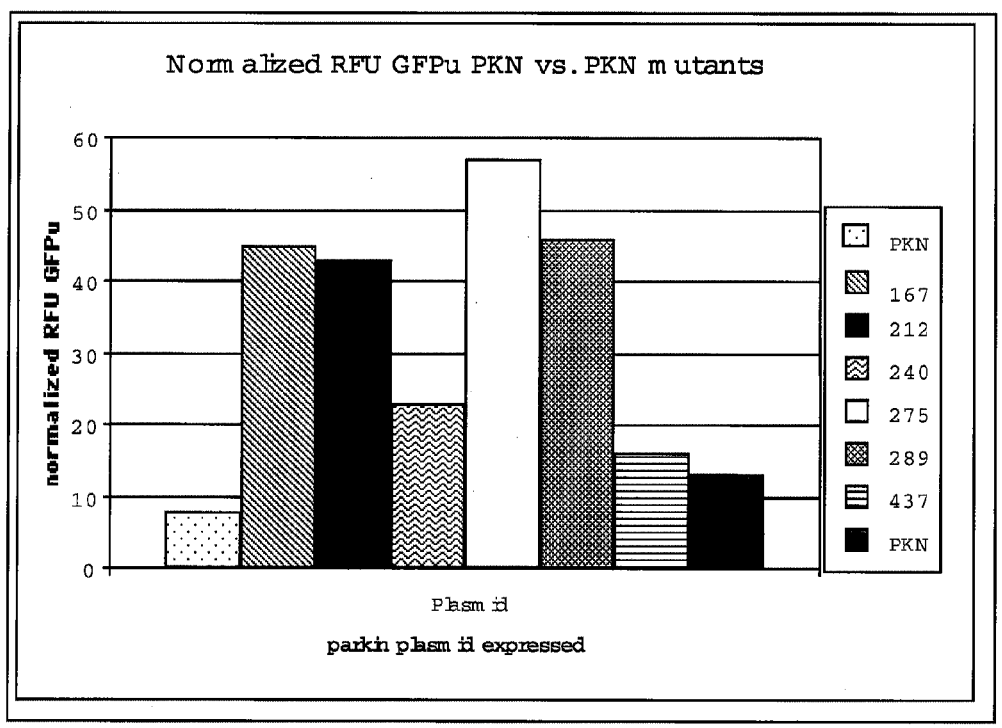
FIG. 3 shows FACscan analysis of GFPu levels in cells expressing GFPu and transfected with a vector expressing Parkin or a Parkin mutant (2 ug DNA). The bar graph shows GFPu levels 2 days post-transfection. Mutants 167, 212, 275 and 289 decreased proteasome activity above the wild-type Parkin (PKN).

Genetic data have established that in humans loss of Parkin protein results in the progressive loss of dopaminergic neurons in the substantia nigra and eventually to Parkinson's Disease ("PD"). The relevant Parkin activity in dopaminergic neurons is likely to be its E3 ubiquitin ligase activity. The present invention contemplates a therapeutic approach to restore or augment Parkin ligase activity using therapeutic agents, such as small molecules, that can help Parkin achieve or maintain an active conformation. In one aspect, the invention relates methods for identification of agents useful for treating Parkinson's Disease. These methods include cell-based and protein-based assays. These and other aspects of the invention are discussed below.

II. Definitions

The terms "Parkin" and "Parkin protein" are used interchangeably and refer to wild-type Parkin or mutant Parkin.

"Wild-type Parkin" refers to human Parkin having the sequence of SEQ ID NO:2. or mouse Parkin having the sequence of SEQ ID NO:4. Wild-type Parkin can also refer to Parkin variants having mutation(s) that do not affect the ligase activity of Parkin and do not confer a different phenotype when expressed in cells. Sequences of nucleic acids and proteins encoding Parkin and other proteins are provided for the convenience of the reader and can also be found in the scientific literature. However, the practice of the invention is not limited to the specific sequences provides. It will be appreciated that variants also can be used in place of the sequences provided.

"Parkin mutant" or "mutant Parkin" refer to a Parkin protein with a sequence that deviates from SEQ ID NO:2 by a substitution, insertion or deletion of one or more residues, and has a different activity or confers a different phenotype than is conferred by wild-type Parkin. When referring to Parkin mutants, conventional nomenclature is used. For example, the R275W mutant has a substitution of tryptophan (W) for arginine (R) at position 275. Generally "Parkin mutant" refers to naturally occurring mutant proteins including, for example, R42P, S167N, C212Y, T240M, R275W, C289G, and P437L.

As used herein, reference to an "agent useful for treating Parkinson's Disease" or "candidate compound for treatment of Parkinson's disease" refers to a compound identified as being more likely than other compounds to exhibit therapeutic or prophylactic benefit for patients with Parkinson's disease, i.e., a drug candidate. It will be understood by those familiar with the process of drug discovery that a drug candidate may undergo further testing (e.g., in vivo testing in animals) prior to being administered to patients. It will also be understood that the therapeutic agent may be a derivative of, or a chemically modified form of, the drug candidate.

III. Identification of Agents Useful for Treating Parkinson's Disease

It has been discovered (see Examples below) that over-expression of wild-type Parkin in cells inhibits proteasome activity and can lead to the deposition of large insoluble inclusions of Parkin protein. Analysis of brain tissue showed that in PD patients Parkin levels appear to be elevated relative to healthy brain tissue and enriched in the insoluble fraction. See Example 5. Without intending to be bound by a particular mechanism, it is believed, based in part on experiments described in the Examples, that the wild-type Parkin protein is prone to misfolding, and that accumulation of misfolded Parkin results in: (1) impairment of proteasome activity, (2) generation of aggresomes containing Parkin and other cell proteins, (3) cell morbidity; and (4) loss of Parkin activity. Loss of Parkin activity is a direct mechanism leading to PD (Kitada et. al., 1998, *Nature* 392:605-608) and point mutations described in this work may also be related to the loss of function of Parkin leading to disease (Foroud et al., 2003, *Ann. Neurology* 60:796-801).

Moreover, it has been discovered that agents that stabilize Parkin (i.e., maintain Parkin in an active conformation even when over-expressed) or induce proper folding of misfolded Parkin are useful therapeutic agents for treatment of Parkinson's Disease. The present invention provides, inter alia, drug screening assays based, in part, on this discovery.

The invention provides both cell-based and protein based assays for such therapeutic agents.

A. Cell-Based Assays

As described in Examples 1-3, in cells in which wild type Parkin is over expressed, aggresomes (or "Parkin inclusions") are formed and proteasome activity is decreased. In HEK293 cells in culture, Parkin protein is expressed endogenously at low levels. At this endogenous level of expression, the protein does not detectably affect the proteasome pathway, other than by performing its normal ligase activity. However, when Parkin protein is recombinantly expressed from a cDNA driven by an heterologous promoter (i.e., is expressed at high levels in cells compared to normal endogenous expression) Parkin protein, at least some of which is misfolded and/or insoluble, interferes with proteasome function. It is possible that the proteasome inhibition characteristic of high levels of Parkin expression also occurs at a much lower level under normal expression conditions. The slow accumulation of misfolded Parkin protein as an insoluble fraction in brain cells may occur over a long period (e.g., 40-80 years) leading to pathology.

Based in part on this discovery, the invention provides cell-based assays for identifying a candidate compound for treatment of Parkinson's Disease. In one assay of the invention, agents that stabilize Parkin or induce proper folding can be identified by the effect of the agent on aggresome formation and/or proteasome function in a cell.

In one embodiment, the assay includes screening for a candidate compound for treatment of Parkinson's Disease by (a) obtaining mammalian cells expressing Parkin; (b) exposing a cell to a test agent; and (c) comparing proteasome function in the cell exposed to the test agent with proteasome function in similar (control) cell not exposed to the test agent. An increased level of proteasome function in the cell exposed to the test agent compared to the control cell indicates the agent is a candidate compound for treatment of Parkinson's Disease. An exemplary assay is described in Example 6. In some assays, cells not expressing exogenous Parkin are used in controls.

As discussed in more detail below, in various embodiments of this assay, the cells used may express wild-type Parkin or mutant Parkin. Preferably the level of expression is higher than the normal level for the particular cell used in the assay. In cases in which recombinant Parkin is expressed in a stably or transiently transfected cell, the expression level will essentially always be higher than normal. This is because endogenous levels of Parkin in cells are low and recombinant expression in which Parkin expression is driven by a heterologous (inducible or constitutive) promoter is comparatively high. Levels of Parkin expression in transfected or non-transfected cells can be measured using routine methods (e.g., immunostaining). Parkin (or other protein) over-expressed in a cell is referred to as "exogenous." Generally cells expressing exogenous proteins are obtained by transfection of the cell with a recombinant DNA encoding the protein. Alternatively, expression of the endogenous parkin gene can be increased by replacing or modifying the native promoter.

In general, as described herein and illustrated in the Examples, Parkin expressing cells express exogenous Parkin but do not express another exogenous mammalian protein. In one example, Parkin expressing cells express exogenous human Parkin but do not express another exogenous human protein. As described herein and illustrated in the Examples, non-mammalian or non-human proteins (e.g., GFP or antibiotic resistance proteins) often are present.

In certain embodiments semi-automated high-throughput methods are used to screen large numbers of test agents in assays of the invention, including parallel or simultaneous analysis of multiple test agents (e.g., a plurality, i.e., at least 5, preferably at least 10, sometimes at least 25, sometimes at least 100 agents).

A.1 Proteasome Function Assays

The effect of an agent on proteasome function in cells can be assessed using any assay of proteasome function. A primary proteasome function is degradation of intracellular proteins. In one embodiment of the assay, Parkin is expressed in a cell that also expresses a reporter-degron fusion protein, and the reporter is used to measure proteasome activity. The fusion protein includes a detectable polypeptide sequence with a degradation signal ("degron") added to the C-terminus (or the N-terminus) of the protein. For illustration and not limitation, an exemplary degron sequence is provided as SEQ ID NO:9. The degradation signal serves to target the polypeptide to the proteasome where the polypeptide is degraded. When the activity of the proteasome is compromised, the levels of polypeptide in the cell increase relative to a cell in which the polypeptide is degraded by a normally functioning proteasome. An increase in protein levels can be detected in a variety of ways.

In one embodiment, proteasome function is assayed in cells using a GFPu reporter system. In the GFPu reporter system, cells that express a green florescent protein (GFP) with a degradation signal added to the C-terminus of the protein are used (see, Bence et al., 2001, *Science* 1552-55; Gilon et al., 1998, *EMBO Journal* 17:2759-66; SEQ ID NOS:6 and 9). As explained above, when the activity of the proteasome is compromised, the levels of GFP in the cell increase. An increase in GFP levels can be detected in a variety of ways including measuring GFP fluorescence levels in live cells or cell extracts and/or measuring levels of the GFU protein by ELISA, immunoblotting, and the like.

Other similar reporter systems can be used, for example, in which a reporter protein other than GFP is used and/or a different degron is used. See, for example, Dantuma et al., 2000, *Nature Biotechnology* 18:538-543. A variety of other proteins can be used, including reporter proteins such as Red Fluorescent Protein, Yellow Fluorescent Protein (e.g., Living Colors™ Fluorescent Proteins from Clontech, Mountain View Calif.), beta-galactosidase, luciferase, and the like. Alternatively, any polypeptide sequences detectable by virtue of an activity (e.g., an enzymatic activity that can be measured), antigenicity (e.g., detectable immunologically), a radioactive, chemoluminescent or fluorescent label, or the like. Degrons are known in the art (see, e.g., Gilon et al., 1998, *EMBO Journal* 17:2759-66; Sheng et al., 2002, *EMBO J.* 21: 6061-71; Levy et al, 1999, *Eur. J. Biochem.* 259:244-52; and Suzuki and Varshavsky, 1999, *EMBO J.* 18:6017-26).

In one version ("the basic assay") the cell-based assay of the invention involves (a) transiently transfecting GFPu-expressing cells with an expression vector encoding wild-type Parkin (b) contacting a portion of the transfected cells and/or progeny of the cells with a test agent, and (c) determining whether the rate of degradation of the GFPu protein is increased, and GFPu levels are reduced in the cells contacted with the test agent compared to control cells not contacted with the test agent. Agents that reduce GFPu levels are candidates for further analysis and therapeutic use. It is expected that at least some agents that decrease GFPu levels do so by stabilizing Parkin structure, reducing the amount of misfolded Parkin.

Cell lines expressing the GFPu reporter are available from the ATCC (e.g., HEK-GFPu CRL-2794). Alternatively, cell lines expressing the GFPu reporter or other reporter-degron fusion proteins can be prepared de novo by transforming cells with a plasmid encoding the fusion protein. Any of a variety of cells can be used, including HEK293 cells (ATCC CRL-1573), SHSY-5Y cells (ATCC-2266), COS cells (CRL-1651); CHO cells (ATCC-CCL-61) or other mammalian cell lines. Cells can be stably or transiently transfected. Preferably the cells are stable transfectants for consistency across multiple assays.

In alternative embodiments, the assay can be carried out using cells stably expressing Parkin, and transiently transfected with the reporter-degron protein, or with cells transiently transfected with both Parkin and the reporter.

Expression vectors, methods for transient transfection, and methods for cell culture suitable for the practice of the invention are well known in the art and are only briefly described here. As is well known, expression vectors are recombinant polynucleotide constructs that typically include a eukaryotic expression control elements operably linked to the coding sequences (e.g., of Parkin). Expression control elements can include a promoter, ribosome binding sites, RNA splice sites, polyadenylation sites, and transcriptional terminator sequences. The expression vectors are typically replicable in the host organisms either as episomes or as an integral part of the host chromosomal DNA. Examples of mammalian expression vectors include pcDNA 3.1 (Invitrogen, San Diego, Calif.); pEAK (Edge Biosystems, Mountain View, Calif.); and others (see Ausubel et al., Current Protocols In Molecular Biology, Greene Publishing and Wiley-Interscience, New York, as supplemented through 2005). Commonly, expression vectors contain selection markers, e.g., ampicillin-resistance or hygromycin-resistance, to permit detection of those cells transformed with the desired DNA sequences. "Transfection" refers to a variety of art-recognized techniques for introducing foreign nucleic acid (e.g., DNA) into a host cell, including calcium phosphate or calcium chloride co-precipitation, DEAE-dextran-mediated transfection, lipofection, and electroporation. Cell culture techniques are also well known. For methods, see Sambrook et al. 1989, *Molecular Cloning: A Laboratory Manual,* 2nd Edition, Cold Spring Harbor Laboratory press; and in Ausubel, 1989, supra.

A.2 Cells Expressing Parkin

In a preferred proteasome function assay, cells expressing the reporter-degron fusion protein are transfected with an expression vector expressing Parkin, as described above. In one embodiment the expression vector encodes a wild-type Parkin. For example, the cDNA for human Parkin (NM004562) can be inserted into the HindIII/XbaI sites of the vector pcDNA3.1 (Invitrogen, San Diego Calif.) for use in this assay.

In another embodiment, an expression vector encoding a Parkin mutant is used. As shown in Example 4, expression of certain Parkin mutants results in inhibition of proteasome function. Generally a Parkin mutant for which heterozygosity is correlated to development of PD is used. Proteasome function assays using Parkin mutants can be conducted as described above for wild-type Parkin, except that cells are transfected with an expression vector encoding a Parkin mutant. This proteasome function assay involves exposing a mammalian cell expressing a mutant Parkin to the test compound; comparing proteasome function in the cell exposed to the test compound and proteasome function characteristic of a cell expressing the mutant Parkin not exposed to the test compound. Exemplary Parkin mutants include S167N, C212Y, T240M, R275W, C289G, P437L (see Table 1). In certain embodiments the Parkin mutant used is R275W, C212Y or C289G. Assays using Parkin mutants can be used as an alternative to, or in combination with, assays using wild-type Parkin.

TABLE 1

| Six Parkin mutations for which heterozygosity is correlated to development of PD | |
|---|---|
| Parkin mutation | Proposed mechanism of pathology |
| S167N | missense mutation/aggresome |
| C212Y | Dominant gain-of-function/aggresome |
| T240M | Loss-of-function |
| R275W | Loss-of-function |
| C289G | Reported to form aggresomes |
| P437L | missense mutation/aggresome |

A.3 Exposing Cell to Test Agents

As described above, Parkin-expressing cells are exposed to a test agent to determine the effect of the agent on proteasome function. Cells expressing a reporter fusion protein (see, e.g., Example 1) are grown and transfected with the Parkin encoding expression construct. Test agent can be added at or after the time of transfection. In one approach test agent is added in media at the time of transfection. In one approach test agent is added after initiation of transfection, e.g., 1 hour to 10 days after transfection, often 2-3 days after transfection. Example 8, below, describes an approach used for automated assays in which test agent is added about 3 hours after transfection. In one embodiment test agent is added to an aliquot of cells about 2 to about 4 hours after transfection.

A variety of classes of test agents can be used. For example, a number of natural and synthetic libraries of compounds can be used (see NCI Open Synthetic Compound Collection library, Bethesda, Md.; chemically synthesized libraries described in Fodor et al., 1991, *Science* 251:767-773; Medynski, 1994, *BioTechnology* 12:709-710; Ohlmeyer et al., 1993, Proc. Natl. Acad. Sci. USA 90:10922-10926; Erb et al., 1994, Proc. Natl. Acad. Sci. USA 91:11422-11426; Jayawickreme et al., 1994, Proc. Natl. Acad. Sci. USA 91:1614-1618; and Salmon et al., 1993, Proc. Natl. Acad. Sci. USA 90:11708-11712). In one embodiment, the agent is a small molecule, e.g., a "chemical chaperone," such as a molecule with a molecular weight less than 1000, and often less than 500.

The duration of the exposure to test agent can vary but will usually be from 1-2 days, although longer (e.g., up to 72 hours or longer) or shorter times (e.g., 4 to 16 hours) can be used. In some embodiments cells are exposed to test agent for about 30 to about 48 hours, or from about 40 to about 50 hours. In an automated approach shown in Example 8, cells are cultured with test agent for 45 hours and assayed. In one approach, cells are transfected, cultured overnight and then exposed to test agent for 33 hours. In one approach, cells are transfected, cultured for 3 hours, and then exposed to test agent for 45 hours.

Similarly, a variety of concentrations of agent can be tested. It will be appreciated that the concentration will vary depending on the nature of the agent, but is typically in the range of 1 nM to 5 uM. Typically several different concentrations of test agent are assayed (e.g., 1 nM, 10 nM, 100 nM, 1 µM, 10 µM and 100 µM) along with a zero concentration control.

The proteasome function of a Parkin-expressing cell contacted with test agent can be compared with proteasome function characteristic of a cell expressing Parkin but not exposed to the candidate compound. Typically this is accomplished by conducting parallel experiments using cells exposed to the test agent (at various concentrations) and cells not exposed to the test agent. That is, proteasome function in cells is measured in the presence or absence of compound. Alternatively, proteasome function in test cells can be compared to standard values obtained previously for proteasome function in cells. In another variation, proteasome function is measured in the same cells before and then after addition of the test agent.

At the end of the culture period, proteasome function can be measured. For example, in GFPu-expressing cells, GFPu fluorescence and/or GFPu quantity can be measured. Measurements may be quantitative, semiquantitative and/or comparative.

It will be apparent to the reader that modifications of the basic assay can be made. For example, culture plates of various types (e.g., 6, 24, 96, or 384 well plates) or other high through-put devices can be used can be used for cell culture, optionally in combination with robotic devices, with concomitant adjustment of plasmid quantity in the transfection.

In one embodiment of the invention, HEK293 GFPu cells are grown to 75% density in culture wells of a six-well cell culture plate (e.g., each well approximately 30 mm in diameter). The cells are transfected the Parkin expression vector described above, using approximately 2.5 ug of plasmid per well, and the cells cultured for about 3 days (e.g., 2, 3, 4 or 5 days) prior to analysis with a test agent.

A.4 Proteasome Function Assays to Determine Whether the Effect of an Agent is Specific for Parkin Proteasome function assays to establish Parkin specificity can be conducted by using the basic assay described above for wild-type Parkin, except that rather then expressing exogenous Parkin, cells are transfected with an expression vector encoding a different protein, e.g., a different protein believed to be prone to misfolding. For example, the Huntingtin (Htt) protein (SEQ ID NO:11) or CFTR (SEQ ID NO:10; accession number NM000492) proteins may be used. Other proteins prone to misfolding that may be used in this assay include superoxide dismutase-1 (SOD1), Rhodopsin, connexin 43, $Ub^{+1}$ (mutant form of ubiquitin), and presenilin. Protein and nucleic acid sequences for these and other suitable mammalian (e.g., human) proteins are known and publically available. This proteasome function assay involves exposing a mammalian cell expressing the non-Parkin protein (e.g., Huntingtin), and not transfected with exogenous parkin) to the candidate agent and comparing proteasome function in the cell with proteasome function characteristic of a cell expressing the non-Parkin protein not exposed to the candidate agent. An agent that stabilizes or increases proteasome function in cells expressing Parkin but not cells expressing the non-parkin protein or other proteins, or which stabilizes or increases proteasome function to a significantly greater degree (e.g., as least a 2-fold difference and preferable at least a 10-fold difference) in the Parkin-expressing cells is likely specifically modulating the effect of Parkin on proteasomes. An agent that stabilizes or increases proteasome function in cells expressing a non-parkin protein, such as Huntingtin, or other proteins as well as in cells expressing Parkin may be acting nonspecifically.

A.5 Parkin Aggregation Assays

In one embodiment, the assay includes screening for a candidate compound for treatment of Parkinson's Disease by (a) obtaining mammalian cells expressing wild-type or mutant Parkin; (b) exposing a cell to a test agent; and (c) comparing Parkin aggregation in the cell exposed to the test agent with Parkin aggregation characteristic of a control cell not exposed to the test agent. A reduced level of Parkin aggregation in the presence of a test agent indicates the agent is a candidate compound for treatment of Parkinson's Disease. In one embodiment the mammalian cells express wild-type Parkin. In one embodiment the mammalian cells express a mutant Parkin. In some cases the mutant Parkin is S167N, C212Y, T240M, R275W, C289G, P437L. Preferably R275W, C212Y or C289G is used.

B. Parkin Binding Assays

An expected characteristic of many chemical chaparones is that they bind to the protein target. Thus, candidate agents useful for treatment of Parkinson's disease can be identified using a Parkin binding assay. The binding assays usually involve contacting purified Parkin protein with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet and Yamamura, 1985, "Neurotransmitter, Hormone or Drug Receptor Binding Methods," in Neurotransmitter Receptor Binding (Yamamura, H. I., et al., eds.), pp. 61-89. The Parkin protein utilized in such assays can be from mammalian cells (recombinant or naturally occurring) or purified Parkin from recombinant bacterial cells.

C. Parkin Activity Assays

Parkin is an ubiquitin ligase (Shimura et. al., 2000, *Nature Genetics* 25:302). Ubiquitin ligase activity is defined by the ability of a protein to recognize a specific ligase substrate, and interact with an E2 enzyme to transfer an ubiquitin molecule from the E2 to the substrate. Ligase activity has been shown to be regulated by accessory proteins, but can also occur with the ligase alone (see Joazeiro and Weissman, 2000, *Cell* 102: 549-52).

In one embodiment, an in vitro assay used to determine whether a candidate agent is useful for treating Parkinson's disease includes measuring the effect on Parkin ligase activity. In an embodiment the ligase activity is the autoubiquitination activity of a purified Parkin protein in the presence of the compound, and comparing the autoubiquitination activity of purified Parkin protein in the presence of the compound with autoubiquitination activity of purified Parkin protein in the absence of the compound. The ability of an agent to increase autoubiquitination activity is indicative of an agent useful for treating Parkinson's disease and a candidate for further testing. In addition, agents that stimulate autoubiquitination activity may increase the affinity of ligase for substrate, or prevent intracellular turnover of Parkin protein, and are therefore of interest for those activities as well. Other Parkin substrates may be used in assays of E3 activity include S5a, Sept4 and troponin I. Parkin E3 activity can be assayed using art-known methods. For illustration, autoubiquitination assays are described below.

C.1 Assays Using Immobilized Parkin

In the immobilization assay, recombinant or purified Parkin is immobilized on a surface (such as a microwell plate, sepharose beads, magnetic beads, and the like) and incubated with a ligase reaction mix that includes ubiquitin. The level of ubiquitination of Parkin under the assay conditions is determined as a measure of Parkin autoubiquitination activity.

Any method for immobilizing Parkin that does not interfere with Parkin activity can be used. In one embodiment, Parkin is immobilized in wells of a 96-well or 386-well microwell plate. Microwell plates are widely available, e.g., from Immulon (Waltham, Mass.) and Maxisorb (Life Technologies, Karsruhe, Germany). Parkin can be immobilized using an antibody binding system in which an antibody that recognizes Parkin is immobilized on a surface, and Parkin is added and captured by the antibody. Alternatively the antibody can recognize an epitope tag fused to the Parkin protein (e.g., His, GST, Flag, Myc, MBP, and the like). An antibody is selected that does not interfere with Parkin enzymatic activity. Methods for antibody-based immobilization and other immunoassays are well known (see, e.g., Harlow and Lane, 1988, Antibodies, A Laboratory Manual, Cold Spring Harbor Publications, New York). In an other approach, Parkin protein with a N-terminal $His_6$ tag can be immobilized using a nickel-coated assay plate.

After a blocking step, a ligase reaction mix including E1 (ubiquitin-activating enzyme, optionally epitope tagged, as with GST or $His_6$), E2 (ubiquitin conjugating enzyme), ATP-Mg, and ubiquitin (usually labeled ubiquitin) is combined with immobilized Parkin (Parkin E3 ligase). Purified ubiquitin pathway enzymes can be obtained commercially (e.g. from Boston Biochem Inc., 840 Memorial Drive, Cambridge, Mass. 02139) or prepared as described in Wee et al., 2000, *J. Protein Chemistry* 19:489-498). Blocking to reduce nonspecific binding of E1 to the plate can be with SuperBlock (Pierce Chemical Company, Rockford, Ill.); SynBlock (Serotec, Raleigh, N.C.); SeaBlock (CalBiochem, Darmstadt, Germany); metal chelate block (Pierce Chemical Company, Rockford, Ill.); 1% casein; glutathione; and various combinations of these, with 1% casein preferred in some embodiments. After the blocking step, the wells can be washed with SuperBlock wash (Pierce Chemical Company, Rockford, Ill.) or Ligase buffer wash (50 mM HEPES/50 mM NaCl). In one embodiment, Immulon 96 or 384 well plates are blocked with 1% casein in 50 mM HEPES/50 mM NaCl and washed using 50 mM HEPES/50 mM NaCl/4 mM DTT.

An exemplary reaction mix is:

| | |
|---|---|
| 1:1 Biotin:ubiquitin | 500 nM |
| GST-E1 | 2-6 nM |
| E2 (UbcH7) | 300 nM |
| Parkin protein | 2-10 ug |
| MgATP | 10 mM |
| Buffer | 50 mM HEPES/ 50 mM NaCl/pH 8.8 |

Parkin protein can be recombinant (e.g., expressed in *E. coli*) or purified. The assay can be carried out at 37° C. for 1 hour and stopped by washing wells with 50 mM HEPES/50 mM NaCl. ATP can be omitted from certain samples as a negative control. In one embodiment, the assay carried out in a 96 or 384 well plate format. The plate is incubated for a period of time (e.g., 60 minutes at room temperature or 40-60 minutes at 37° C.). Plates are washed to remove soluble reagents and the presence or amount of ubiquitin (i.e. the ubiquitin component of autoubiquinated Parkin) is determined.

Methods for detection of ubiquitin will depend on the label or tag used. For example, in a plate assay, fluorescein-tagged ubiquitin, can be detected directly using a fluorescence plate reader, biotin-tagged ubiquitin can be detected using labeled strepavidin (e.g., strepavidin-HRP or 1:5000 Neutravidin-HRP [Pierce Chemical Comp. Rockford, Ill.]), and epitope-tagged ubiquitin can be detected in an immunoassay using anti-tag antibodies. Epitope tags are fused to the N-terminus of ubiquitin or otherwise attached in a way the does not interfere with ubiquitination. These assays and other useful assays are well known the in art.

C.2 Assays Using Parkin in Solution

In an alternative approach, the autoubiquitination assay for Parkin is carried out in solution and then the solution (or an aliquot) is transferred to a capture plate for quantitation. In an exemplary reaction, the reaction components (below) are assembled in 50 microliter volume and the assay is run for from 10 to 90 minutes (e.g., 60 minutes) at 37° C.

Reaction Components:
50 mM HEPES/50 mM NaCl/pH 8.8
500 nM 1:1 Biotin:ubiquitin
2-6 nM GST-E1
300 nM E2 (UbCH7)
2-10 ug *E. coli* recombinant Parkin protein
10 mM MgATP*

*Can be added last to initiate the reaction.

After reaction is complete, the reaction mix is transferred to a capture plate (e.g., 96 or 384 well plate) containing an immobilized moiety that binds Parkin (e.g., anti-Parkin antibody, nickel for His-tagged Parkin, or anti-epitope tagged antibody such as anti-flag GST, His, Myc, MBP, etc. for epitope-tagged Parkin). When nickel plates are used to immobilize His-tagged Parkin the reaction may be stopped by the addition of 6M Guanidinium HCl. This capture plate can be blocked with 1% casein. The reaction mix is incubated in the capture plate for 60 minutes. After this time, the plate is washed 3× with 50 mM HEPES/50 mM NaCl/4 mM DTT). Detection is carried out using a reagent that binds to the tag present on the ubiquitin moiety (e.g., strepavidin-HRP) and processed using standard procedures.

C.3 Assays Using Parkin Substrates

In another approach ubiquitination of a Parkin substrate is measured to determine E3 activity. In one approach, a substrate (e.g., Sept4) is immobilized on a surface (such as a microwell plate, Sepharose beads, magnetic beads, and the like) and incubated with a ligase reaction mix that includes Parkin, E1, E2, ubiquitin, and ATP. After a blocking step, a ligase reaction mix including E1 (ubiquitin-activating enzyme), E2 (ubiquitin conjugating enzyme), ATP-Mg, ubiquitin (usually labeled ubiquitin) and Parkin (Parkin E3 ligase) is combined with an immobilized Sept4 protein. Optionally E1 is epitope tagged (e.g., with GST or His$_6$). The reaction components can be added in any desired order. ATP can be added last, if desired, to initiate the reaction. An exemplary reaction mix is: Parkin protein (e.g., 2-10 µg), 500 nM 1:1 Biotin:ubiquitin (biotinylated ubiquitin), 2-6 nM GST-E1, 300 nM E2 (UbCH7), 10 mM MgATP, and 50 mM HEPES/50 mM NaCl pH 8.8.

D. Combinations of Assays

The cell-based and protein-based assays described above can be used independently or in various combinations to identify candidate compounds for treatment of Parkinson's Disease that reduce proteasome impairment in cells expressing Parkin proteins. In one embodiment, the "basic assay" for agents that ameliorate the inhibition of proteasome function in cells expressing wild-type Parkin can be used in combination with additional assays such as: (1) proteasome function assays using Parkin mutants (2) Parkin aggregation assays (3) proteasome function assays to establish Parkin specificity (4) Parkin binding assays (5) in vitro protein activity assays. When used in combination, these assays can be conducted in any order. For example, initial high-throughput screening can be conducted using an in vitro protein assay and the basic cell-based assay can be used as a secondary screen. Alternatively, for example, cell-based assays can be conducted first and in vitro protein binding and activity assays can be used as a secondary screen. Other sequences and combinations of assays will be apparent to the reader.

In one embodiment agents that rescue proteasome function both in cells expressing wild-type Parkin and in cells expressing a mutant Parkin are identified as particularly promising drug candidates and subjected to further testing. In one embodiment agents are selected that rescue proteasome function in multiple cell lines, such as cells expressing proteins selected from wild-type Parkin and mutant Parkins (e.g., R275W, C212Y and C289G).

In one aspect of the invention, combinations of different cell-based assays and protein based assays are used to screen for agents useful for treatment of Parkinson's disease. For example, the basic cell based assay using wild-type Parkin can be using in conjunction with any one or combination of assays described above. Solely for illustration and not for limitation exemplary combinations of assays (and exemplary, non-limiting, profiles of agents considered useful) are shown in the table below. For example, one screening approach (C) comprises two assays: the cell based assay with wild-type Parkin and the Parkin activity assay. These assays can be conducted in any order.

TABLE 2

|  | A | B | C | D | E | F |
|---|---|---|---|---|---|---|
| 1. Basic cell based assay with wild-type Parkin | + | + | + | + | + | + |
| 2. Basic cell based assay with mutant Parkin | + | − |   |   | + |   |
| 3. Specificity assay | ++ | ++ |   |   |   | ++ |
| 4. Protein binding assay | * |   |   |   |   |   |
| 5. Protein activity assay | ** |   | ** |   |   |   |

+ Increases proteasome function
− Does not increase proteasome function
++ Does not increase proteasome function in nonParkin expressing cells
* binds
** increases ligase activity V. Examples Example 1

GFPu HEK293 Cells

GFPu-expressing cell lines were prepared as follows: HEK293 cells (ATCC No. CRL-1573) were transformed using a construct in which an oligonucleotide encoding a short degron (Gilon et al., 1998, EMBO Journal 17:2759-66) is inserted C-terminal to coding sequence for GFP (Heim et al., 1994, Proc. Nat. Acad. Sci. USA 91:12501-504; Accession #P42212). Cells were transfected with 2 ug cDNA. The cells were cultured for 48 hours and transformants were selected using 1000 ug/ml G418 (geneticin). After an additional 7 days, the cell growth media (DMEM plus 1000 ug/ml G418) was changed by removing old media and adding fresh media. Cells were allowed to grow for two weeks to select for cells that were resistant to G418. These cells were then collected and sorted by FACS techniques to identify and isolate single cells. These single cells were individually sorted into 96-well plates and allowed to grow and proliferate over two week period. The cells were then plated into duplicate 96 well plates. One plate was analyzed by FacScan the other plate was used to expand clones that were identified as positive in the FacScan analysis.

Clones were screened for very low background levels of GFP and an increase of more than 2 log units of fluorescence in the presence of the proteasome inhibitor epoxomicin. Two GFPu expressing cell lines, lines 60 and 61, were used in the remainder of the experiments.

Cells from the two GFPu cell lines were grown to 75% density in six-well plates, transfected with 2.5 ug per well of cDNA expression vectors encoding Parkin, Parkin mutants, Synuclein, or Synuclein variants. The cells were cultured for 2-5 days and examined using fluorescence microscopy and FACScan to measure GFP fluorescence. In some cases, epoxomicin was added 5 hours prior to FACScan as a positive control for GFPu levels. In addition, cell extracts were prepared for immunoblotting.

Example 2

Expression of Wild-Type Parkin Results in Parkin Inclusions and Decreases in Proteasome Activity in GFPu-Expressing Cell Lines In both of the GFPu cell lines (lines 60 and 61), the overexpression of Parkin resulted in formation of Parkin aggregates, as determined by immunoblotting and microscopy. Parkin transfection also resulted in a striking increase in GFPu levels, indicating that expression or overexpression of Parkin impaired proteasome activity. FIGS. 1A and 1B show an immunoblot from cell line 60. GFPu/293 cells were transfected with pcDNA3.1 vector (lanes 1 and 2) or with pcDNA3.1-Parkin (lanes 3 & 4). 48 hours post transfection, cells were extracted for soluble protein and insoluble protein and these extracts were analyzed by immunoblotting for GFPu (bottom panel; FIG. 1B) or Parkin (top panel; FIG. 1A). Soluble protein extract (lanes 1 and 3); insoluble protein extract (lanes 2 and 4). These data demonstrate a clear accumulation of GFPu protein after Parkin expression (compare lanes 3 & 4 with lanes 1 & 2), and also demonstrate the distribution of GFPu protein into the insoluble protein fraction after Parkin overexpression (compare lane 4 with lane 3).

Example 3

Overexpression of Parkin, but not Synuclein, Results in Aggresomes

FIG. 2 shows epifluorescent and immunofluorscent images illustrating that expression of Parkin protein leads to stabilization and aggregation of other proteasome substrates such as GFPu. Parkin cDNA was transfected in to GFPu 293 cells prepared as described in Example 1 alone (Panels A and B) or with cDNA for alpha-synuclein and Parkin cDNA (Panels C, D and E). The cells were fixed after 48 hours and processed for immunofluorescence microscopy. Parkin protein was localized by staining with antibody HPA1A to residues 85-96 of human Parkin protein, alpha-synuclein was localized by staining with Syn-1 antibody (Transduction labs, San Jose, Calif.), and GFPu was localized based on the green fluorescence of the protein.

In cells expressing Parkin, Parkin protein (Panel A, arrows) is found as aggregates in the cells, and is colocalized with aggregates or accumulation of GFPu (Panel B, arrows). In cells not expressing Parkin protein (asterisk) there was no accumulation of GFPu.

In cells expressing both Parkin and alpha-synuclein, alpha-synuclein does not aggregate and is not required for the Parkin-mediated increase in GFPu. Arrows show that in cells expressing both synuclein and Parkin, aggregates of Parkin (Panel C) and GFPu (Panel D), but not of alpha-synuclein (Panel E), are found. Arrowhead indicates cells expressing only Parkin. The # symbol identifies a cell expressing alpha-synuclein but not Parkin. This cell does not have an increase in GFPu, indicating synuclein is not sufficient to increase GFPu. It is clear from this that the GFPu is accumulated/aggregated in cells expressing Parkin, and alpha-synuclein is not required.

Example 4

Expression of Mutant Parkins Heterozygous "Dominant" Parkin Mutations

Expression plasmids encoding (1) wild-type Parkin or (2) mutant Parkin for which heterozygosity is correlated to development of PD were transfected into HEK 293/GFPu cells to assess the effect of the mutant Parkin proteins on proteasome function and aggregation (see Table 1).

FIG. 3 shows the results of FACscan analysis 2 days post transfection. Inhibition of proteasome activity was significantly higher with mutants S167N, R275W, C212Y and C289G than for wild-type Parkin. Mutants R275W, C212Y and C289G significantly reduced proteasome activity at all times and transfection concentrations tested.

Figure 4:
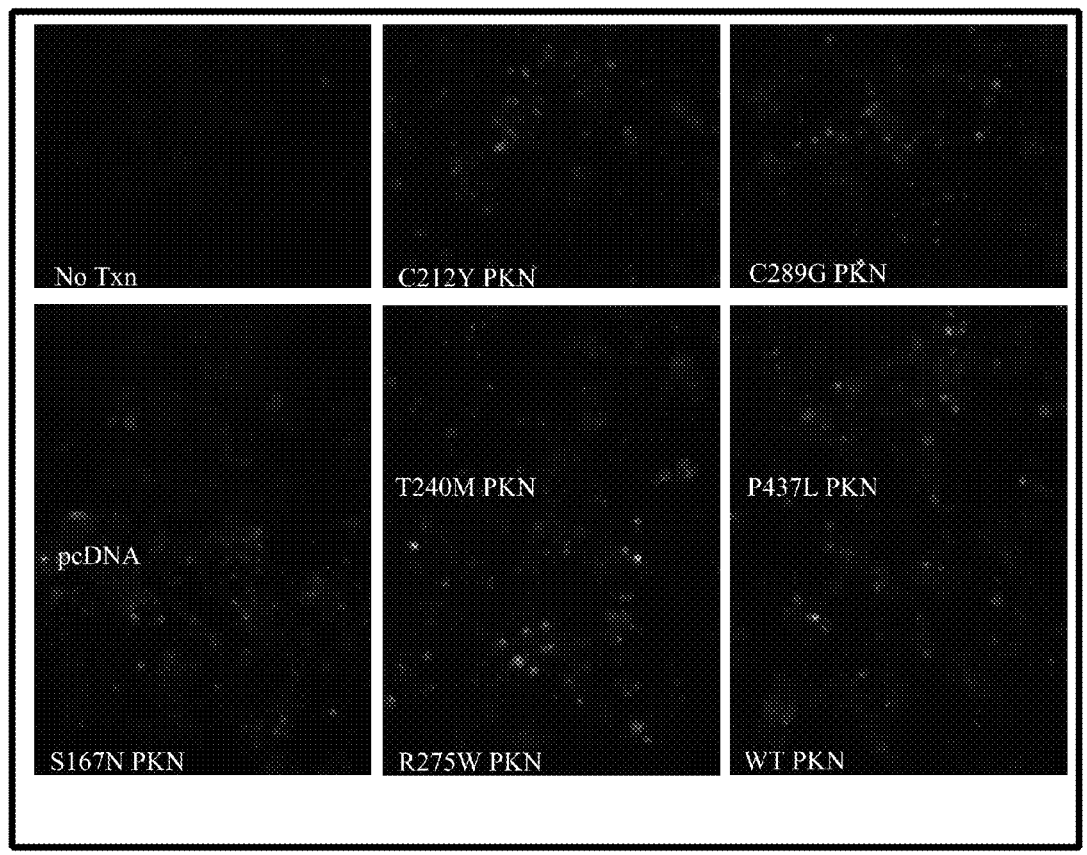
FIG. 4 shows formation of GFPu aggresomes after expression of various Parkin mutant cDNAs in HEK293/GFPu cells. Cells were transfected with 2 ug cDNA and five days later epifluorescence images of each sample were recorded using the same camera settings for each sample to reflect the level of fluorescence intensity. Fluorescence intensity is a direct measure of GFPu levels in the cells.

FIG. 4 shows epifluorescence images of each sample five days after transfection of the HEK 293/GFPu cells. The images were recorded using the same camera settings for each sample to reflect the level of fluorescence intensity, a direct measure of GFPu levels in the cells. As shown in the figure, expression of Parkin mutants can force GFPu into an aggresome. As shown in FIG. 4, and confirmed in experiments using an ArrayScan® high content screening device (data not shown), expression of mutants S167N, R275W, C212Y and C289G increased GFP levels (i.e., significantly reduced proteasome activity).

Example 5

Parkin Distribution in Human Brain Tissue

The location and characteristics of Parkin protein in human brain tissue from sporadic PD patients and healthy controls was determined by immunoblotting of brain extracts.

Methods: Brain tissue from sporadic PD and normal individuals was obtained from the UCLA brain bank. Each sample consisted of tissue from four brain regions: Frontal cortex, caudate nucleus, putamen and substantia nigra. The later three brain regions are components of the nigrostriatal pathway. Frozen brain tissue from each brain region was homogenized via dounce, and extracted at a ratio of 0.5 mg tissue/1 ml of IPB extraction buffer (50 mM Tris 7.5; 300 mM NaCl; 0.05% Deoxycholate; 0.1% NP-40, 5 mM EDTA). After 20 minutes on ice, homogenates were spun for 10 minutes at 10,000×g. This supernatant was removed and the pellet was extracted again in the same manner, and centrifuged again. This second IPB supernatant was removed and the final remaining pellet was then solubilized in 1% SDS/10 mM Tris 7.5 for ten minutes at room temperature, followed by sonication for 20 seconds.

Figure 5A:
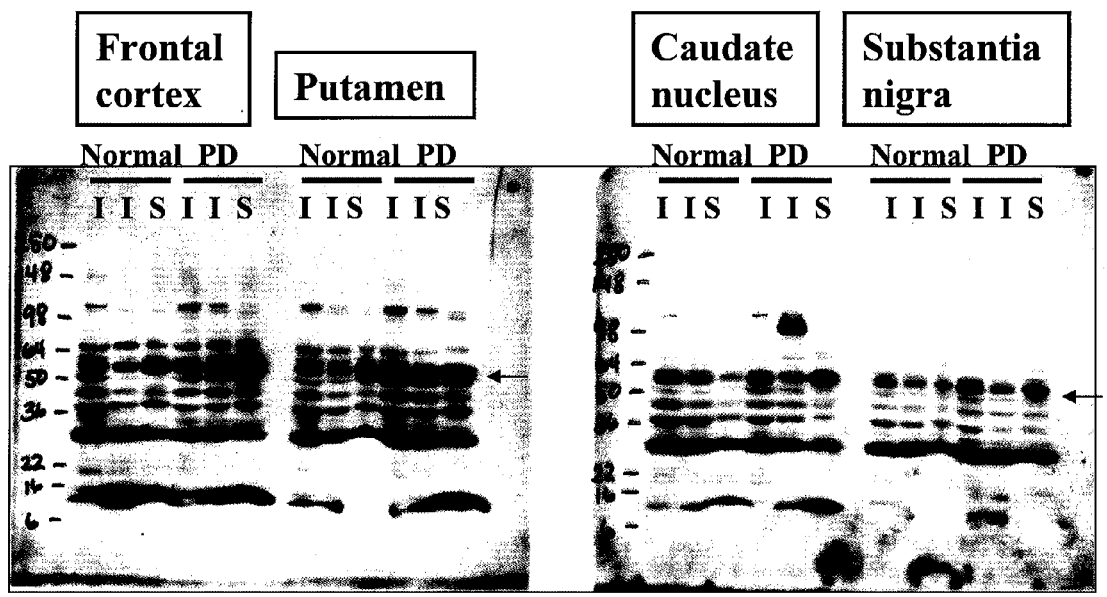
FIGS. 5A and 5B show the distribution of Parkin protein in normal and PD brains.

FIG. 5 shows the distribution of Parkin protein in normal and PD brain. Brain protein was separated electrophoretically and immunoblotting was carried out using HPA1A, a polyclonal antibody to human Parkin residues 85-95. In FIG. 5A (I) is the IPB fraction and (S) is the SDS fraction, as described above. It is noteworthy that in the PD samples, the amount of 52-kD Parkin protein overall is increased, and the amount of insoluble Parkin is also increased.

Figure 5B:
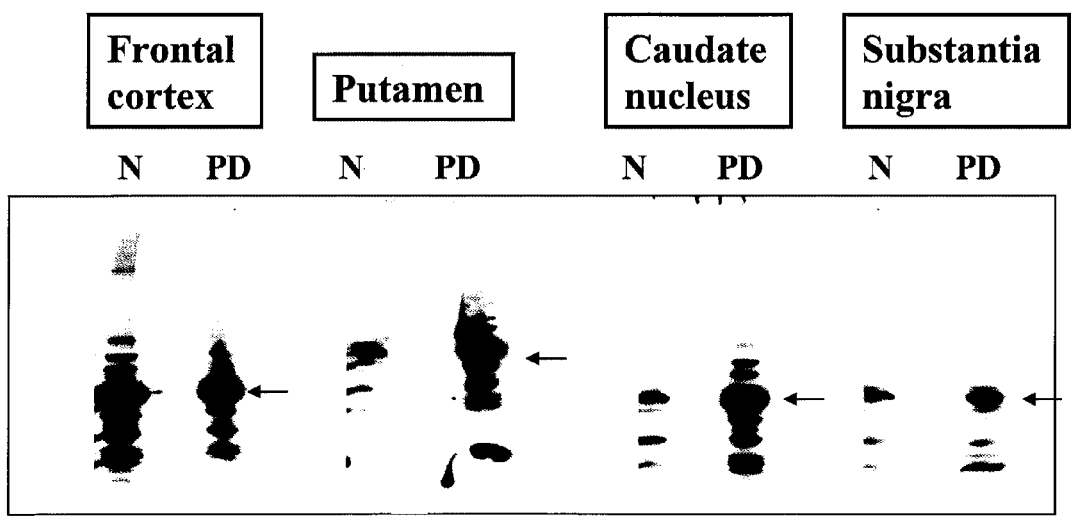

A direct comparison of insoluble material from the same samples is provided in FIG. 5B. Compared to FIG. 5A, there is an accumulation of higher molecular weight material, possibly because the samples were sonicated just prior to loading the FIG. 5B gels, but not the FIG. 5A gels. Although Parkin is increased in the frontal cortex of both samples, it is increased in the nigrostriatal portions of the brain (putamen, caudate nucleus and the substantia nigra) only in the PD patients. The data in FIG. 5 suggest that in sporadic PD patients, Parkin levels may be increased relative to controls overall and enriched in the insoluble fraction. Insoluble protein is highly unlikely to be active.

Example 6

Cell Based Assay

HEK293 cells stably expressing a proteasome-targeted Green Fluorescent Protein (GFP) were transiently transfected with an expression vector expressing wild type Parkin or with a vector only control (pEAK; Edge Biosystems, Mountain View, Calif.). The cells were maintained at 37° C. in 5% $CO_2$ for 16-24 hours. Cells were subsequently fixed with 3.7% formaldehyde and then washed 2× with PBS. Cells were then stained with 1 ug/ml Hoechst dye for 15 minutes at room temperature and then washed 2× with PBS leaving 200 ul of PBS in the well. Cells were imaged on the ArrayScan VTI (Cellomics, Inc.) using the XF100 filter set that had been optimized for GFP. Data were collected from at least 200 cells/well. The Target Activation Bioapplication program was used to analyze intracellular fluorescence ("mean average intensity") where the mask modifier was set at 2 pixels.

Figure 6A:
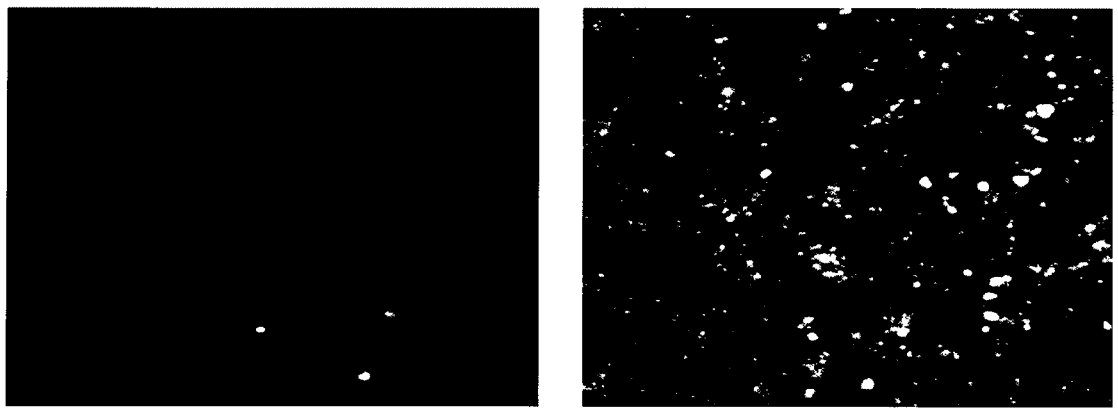
FIGS. 6A and 6B show fluorescent images of cells transfected with a vector control (FIG. 6A, left) or wild type Parkin or (FIG. 6A, right) and the average fluorescence intensities from the cells (FIG. 6B).

FIG. 6A shows fluorescent images of cells transfected with wild type Parkin (upper right) or vector control (upper left). In control transfected cells (vector alone) there was very little fluorescent intensity while in Parkin transfected cells exhibited a marked increase in GFP fluorescence intensity indicative of aggresome formation.

Figure 6B:
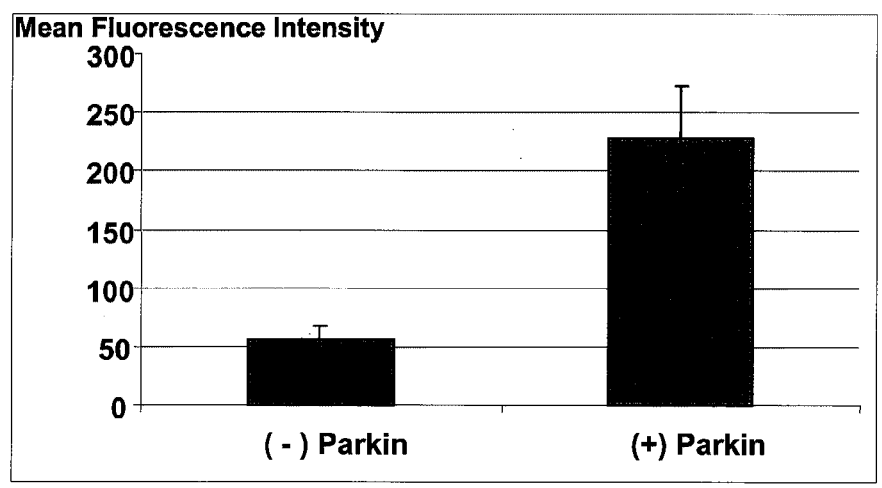

Similar results were observed in a number of different experiments. The signal to background ratio is consistently 3 to 5, where signal is defined as the mean fluorescence intensity from Parkin-transfected cells and background is mean fluorescence intensity from control treated cells (FIG. 6B).

Because the cells are transiently transfected with DNA, we confirmed that there were not large variations in measured fluorescence intensities from well to well. Cells in each well of a 96-well plate were transfected with wild type Parkin and the mean average fluorescence intensity from each well was recorded. The coefficient of variation (CV) across the plate was quite low indicating the screening assay provides reliable consistent results.

A particular cell-based assay for identifying a candidate compound for treatment of Parkinson's Disease can be carried out as follows. Hek293 cells stably expressing a proteasome-targeted Green Fluorescent Protein (GFP) are obtained and are transiently transfected with an expression vector expressing wild type Parkin ("test cells"). Vector only control cells are also obtained. Four equivalent subcultures are prepared from the vector only cells and 16 test subcultures are obtained from the each parent culture. A test agent ("TA#100") is dissolved in culture medium. The test cells are provided with fresh culture medium containing 0, 1, 10, or 100 micrograms TA#100 and cultured under conditions in which Parkin is expressed. After 2 days the cells are fixed and processed as described above. The cells are imaged on the ArrayScan VTI using filters optimized for GFP. Data were collected from at least 200 cells/well. The fluorescence intensity and distribution in cells exposed to various amounts of TA#100 is determined, the fluorescence intensity being a measure of proteasome function in the cells. A decrease in fluorescence in the presence of TA#100 is evidence of an increased level of proteasome function in the cell exposed to the test agent and indicates the agent is a candidate compound for treatment of Parkinson's Disease. Additional assays are carried out to determine the dose-responsiveness of the effect. It will be appreciated that this example is for illustration and the reader guided by this specification will appreciate that there are numerous variations of this particular assay.

Example 7

Optimization and Adaptation of GFPu Assay

This example describes adaptation of the GFPu Assay for automated screening.
a) Cell Density
The first step in assay optimization was to determine the optimal cell density for plating HEK293 cells. Standard 96-well plates were used, having a surface area of about 32.15 mm$^2$. In FIGS. 7A and 7B we show that the optimal cell density for plating was between 8,000-16,000 cells/well. Higher numbers of cells resulted in a much more variable assay with a Z' value of about 0.4 (FIG. 7B). Compounds are usually delivered to cells in DMSO, thus the sensitivity of cells to DMSO must be determined. In FIG. 8, we show that HEK293 cells were not significantly affected by DMSO until the concentration reached 1%, and therefore, we decided to use 0.25% DMSO concentration final in-well for our screening conditions.
b) Transfection and Incubation
In this assay, HEK293 cells were transiently transfected with pEAK vector or wild type Parkin. In FIG. 9, we explored how changing the amount of transfected DNA affected the signal/background (S/B) ratio. In this experiment, cells were transfected with increasing amounts of DNA and then incubated for 48 hours at 37° C. Cells were subsequently fixed with 3.7% paraformaldehyde and then washed 3× with PBS. Cells were stained with 1 ug/ml Hoechst dye for 15 minutes, washed, and then imaged on the ArrayScan VTI using the XF100 filter set that is optimized for GFP. We determined that 0.14 ug of DNA/well (the initial assay conditions) yielded an optimal signal/background ratio; increasing the amount of DNA/well actually decreased S/B ratios (FIG. 10). The Cellomics ArrayScan, with its multi-parametric features, is well-suited to determine the efficiency of transfection. In FIG. 10, parkin transfected cells were stained with Hoechst and with an antibody to parkin to determine transfection efficiency. We observed parkin staining in over 60% of the cells.

The length of time of incubation of cells after transfection can make a large difference in the signal/background ratio as well as the variability in the assay. In FIG. 11, a time course of incubation of cells after transfection with parkin determined that the signal/background was still increasing after 72 hours of incubation. However, we decided to cut the length of incubation to 45 hours, as shortly after this time point, the media would need to be changed. In addition, at the 72 hour time point, there was more variability in the assay (data not shown).
c) Automated Assay
A summary of the finalized automation scheme is outlined in FIG. 12. Briefly, cells were manually transfected with Parkin using the Fugene Reagent (Roche) and then incubated for three hours at 37° C. After three hours of treatment with Fugene, transfection is over 80% complete (Roche personal communication). Compounds were then added to the cell plate at a final concentration of 10 uM using the Multimek™ Automated Pipettor. Compounds were incubated with cells for 45 hours at 37° C. and then the media was gently aspirated with the Multimek. A mixture of 1 ug/ml Hoechst dye and 4% paraformaldehyde were then added to the cells for 40 minutes at room temperature using the Titertek Multidrop™ Lab System. Cell plates were subsequently washed using the Tecan PowerWasher and then read on the Cellomcis ArrayScan. A detailed protocol outlining this process step by step is shown in Example 8. Using this protocol, we commonly achieved Z' values above 0.6 and concomitant S/B ratios above 6 and therefore, the GFPu assay was ready for screening of the LOPAC library.

Example 8

Protocol for GFPu Assay in 96-Well Format

This example describes a protocol for the GFPu Assay in 96-well format. It will be appreciated that the protocol can be readily modified for other multi-well formats and that certain parameters can vary. Generally, the test compound is added to cells when transfection is mostly (at least 85%, preferable at least 90%) complete, typically about 3 hours. Dose-response curves are generated using methods known in the art. Typically, serial 2-fold or 3-fold dilutions (usually in the range 10 uM to 50 pM) are tested.
1) HEK293 cells stably expressing GFP are cultured in DMEM containing 10% FBS, glutamine 2 mM and G418 sulfate at 600 µg/ml.
2) HEK 293 cells are harvested using PBS containing 5 mM EDTA. 180 µl of HEK293 cells at 67,000 cells/ml are then plated onto Costar PDL coated plates (#3667). After seeding cells on the plate, we let them sit for 30 minutes at room temperature in the tissue culture hood before placing them back into the incubator. This treatment may help reduce edge effects and is optional.
3) Incubate the plate overnight at 37° C./5% $CO_2$ in the incubator.
4) A typical transfection cocktail is created as follows: Mix 50 ml of serum free DMEM with 1.087 ml of Fugene and wait 5 minutes at room temperature. Next add 375 µg of Parkin DNA or control vector, gently mix and incubate 35-45 minutes at room temperature. Preliminary results suggest that longer incubations are tolerated.

5) Add 20 µl of transfection cocktail to each well of the plate and place back in the incubator for three hours at 37° C.

6) Add 20 µl of compound to all relevant wells. Final in-well concentration for compound is 10 µM. The DMSO concentration final in-well is 0.2%. Compound plates are diluted using serum free DMEM. All control wells have 0.2% DMSO final concentration in-well.

7) Plates are then incubated for 45 hours at 37° C. and 5% $CO_2$.

8) Aspirate media out of wells.

9) Add 125 of a mixture containing 1 µg/ml Hoechst dye and 4% paraformaldehyde in 0.1M NaPhosphate buffer for 40 minutes at room temperature.

10) Wash with PBS containing calcium and magnesium and leave 200 µl in well.

11) Read on the ArrayScan using the Target Activation Bioapplication.

Materials: HEK293 cells stably transfected with GFP or peak control vector; G418 sulfate from CELLGRO (cat# G1-234-RG); FUGENE Transfection reagent from ROCHE (cat# 11814443001); COSTAR PDL coated plates (cat#3667); and HYCLONE FBS (cat# SV3001403).

Example 9

Screening the LOPAC Library

Screening was carried out using the Library of Pharmacologically Active Compounds (LOPAC) from SIGMA CHEMICAL CO. In addition to screening for the effects of compounds on parkin expressing cells, we carried out a selectivity screen using two different proteins in the GFPu assay, both of which give an increase in GFPu after transfection. The first is the RING finger ligase NRDP1 as a molecule structurally and functionally similar to Parkin. The second is the Cystic Fibrosis Transmembrane Conductance Regulator (CFTR) as a molecule that is a twelve-pass membrane channel protein, and structurally not related to Parkin.

Dose response curves were generated by exposing cells to compounds at various concentrations. Eight 2-fold dilutions were used (10 uM to about 78 nM). Results are provided in Table 3, below. "Hill" refers to the Hill Slope.

Screening of the Library of Pharmacologically Active Compounds (LOPAC) resulted in the identification of hits that largely fell into three major classes of drugs. First, we identified six compounds from the screen that were inhibitors of microtubule assembly and function: ELN475312 (nocodazol), ELN476311 (colchicine), ELN476780 (taxol), ELN476767 (podophyllotoxin), and the vinca alkaloids, ELN477062 (vinblastine) and ELN477063 (vincristine). The fact that we identified these compounds as inhibitors of aggresome formation is not surprising. Microtubules have been shown to play a critical role in the formation of aggresomes (Kopito, 2000, *Trends in Cell Biology* 10, 524-530). Small aggregates, formed at the periphery of cells, are delivered along microtubule tracks on retrograde motors to a perinuclear location at the microtubule organizing center forming aggresomes (Johnston et al. 1998, JCB 143(7), 1883-1898). In that study (Johnston et al., 1998), it was shown that nocodazol, colchicine, and vinblastine completely abrogated aggresome formation. Thus, these findings correlate well with what was observed in our screening campaign and also serve to validate our assay.

The second class of drugs that we identified as hits were a wide variety of kinase and phosphatase inhibitors. It is tempting to speculate that many of these kinases and phosphatases could be regulating microtubule assembly and function. Microtubule Associated Proteins (MAPS) bind to and stabilize microtubule proteins. The binding affinity of MAPS to microtubules can be regulated by the MAP phosphorylation state. We observed that ELN476493 (myricetin), a casein-kinase inhibitor, exhibited 59% inhibition at 10 µM (Table 3) in the GFPu assay yet upon dose-response curve follow-up did not reach the 40% inhibition threshold and will be retested. It has been previously shown that depletion of casein kinase II is accompanied by site-specific dephosphorylation of MAP1B, which is paralleled by a release of MAP1B from microtubules (Ulloa et al., 1993, *EMBO J.* 12(4), 1633-1640). Thus, inhibiting phosphorylation of MAP1B by casein kinase II or other kinases, could interfere with aggresome formation, which is critically dependent on the assembly and proper functioning of microtubules. It has also been shown that PKC controls microtubule-based traffic and that inhibiting PKC may lead to depolymerization of microtubules (Kermorgant et al., 2003, *J. Biol. Chem.* 278: 28921-29). We identified two PKC inhibitors as hits in the GFPu assay, ELN476574 (41% inhibition at 10 µM) and ELN476320 ($IC_{50}$ 2.39 µM), although both exhibited moderate to high cytotoxicty in HEK293 cells. We also observed that ELN476545 and ELN476282, both CDK1 inhibitors, recorded $IC_{50}$ values of 7.5 µM and 0.33 µM respectively in the GFPu assay. This is not surprising as it has been shown that CDKs can modulate retrograde and anterograde axonal transport (Ratner et al., 1998, *J. Neurosci.* 18:7717-26). ELN476646 (Wortmannin), a PI3 kinase inhibitor, also exhibited activity in the GFPu assay $IC_{50}$ 0.75 µM. However, the IC50 of Wortmannin for PI3 kinase is roughly 10 nM (L.W. Bova personal communication) and thus Wortmannin is probably functioning to decrease aggresome formation through effects on other targets. It should be emphasized that although one mechanism by which kinase and phosphatase inhibitors could modulate aggresome formation is by interfering with the phosphorylation state of MAPs, we have not ruled out the possibility that inhibition of various kinases may lead to stabilization of parkin, by whatever mechanism, accounting for decreased aggresome formation.

The third major class of compounds identified as hits in the GFPu screening campaign were DNA crosslinkers, or inhibitors of DNA synthesis and metabolism. ELN476469 (melphalan) and ELN29018 (chlorambucil) are DNA alkylating reagents (crosslinkers) that decreased aggresome formation yet interestingly, did not exhibit much cytotoxicity. ELN29019 (5-fluoruracil), a thymidylate synthetase inhibitor, recorded an IC50 of 9 µM and was characterized as having low cytotoxicity. ELN18065 and ELN476235 are DNA topoisomerase inhibitors with IC50's of 2.1 uM and <0.078 µM respectively. ELN476201 (5-azacytidine) is a DNA methyltransferase inhibitor with an IC50 of 5.36 uM. ELN476809 (methotrexate) is a folic acid analogue, and ELN476491 (mitoxantrone) a DNA synthesis inhibitor, both recorded $IC_{50}$'s of <0.078. Since most of the drugs in this class are solely chemotherapeutic agents, it is unlikely that they represent good candidates to move forward as parkin stabilizing compounds.

Other compounds of interest include ELN476309 (ZPCK) and ELN477056 (TPCK) that are both chymotrypsin inhibitors with $IC_{50}$ values of 4.1 and 9.25 µM respectively in the GFPu assay. It is unlikely that these two compounds are blocking aggresome formation through inhibition of chymotrypsin. However, there may be other serine proteases present in HEK293 cells that are inhibited by ELN476309 and ELN477056 that somehow account for inhibition of aggresome formation. Furthermore, it has been shown that at higher concentrations (25-50 uM) TPCK does inhibit cAMP dependent protein kinase (Kupfer et al., 1979, PNAS 76(7), 3073-3077), 3-PI-dependent kinase 1 (Ballif et al., 2001, JBC 276, 12466) as well as aldehyde dehydrogenase (Dryjanski et al., 1998, Biochemistry 37, 14151-56). Thus TPCK and ZPCK may be inhibiting aggresome formation through off target effects. In addition, it is possible that TPCK and ZPCK could have a direct interaction with parkin that would lead to its stabilization and thus decrease aggresome formation. Hopefully, this possibility will be tested in the next trimester. All the same, ELN476309 and ELN477056 do have good Lipinski properties: MW's, ClogP values, number of H-bond donors and acceptors.

Two compounds known to modulate the cholinergic system were identified as hits in the GFPu screen. ELN476516, a choline acetyl transferase inhibitor, and ELN476478, a nicotinic receptor antagonist recorded IC50 values of 9.0 and 9.9 µM respectively. Is there a cholinergic component that modulates aggresome formation in HEK293 cells? Most likely not, as the Ki value for ELN476478 for the nicotinic receptor is roughly 400 nM, 20 times lower than its IC50 in the GFP assay. In addition, it is not clear whether HEK293 cells even express the nicotinic receptor or have a prominent cholinergic system present. Structurally, both of these compounds are quaternary ammonium containing compounds, and possibly, this feature does play some role in their aggresome inhibiting properties.

Also of note, ELN476182, a 5HT1B antagonist and ELN476489, an irreversible PPAR-γ inhibitor blocked aggresome formation with IC50 values of 8.48 µM and 43% inhibition at 10 µM respectively. However, it is important to keep in mind that the Ki of ELN476182 for the 5HT1B receptor is 2 nM and the Ki of ELN476489 for PPAR-γ is 13 nM. Thus, these compounds are most likely not mediating their effects through the 5HT1B or PPAR-γ receptor families. The exact off-target effects of these compounds may be elucidated next trimester.

In summary, we observed a hit rate of 3.6%, 46 hits out of a total of 1250 compounds screened from the LOPAC library where we set a limit of 40% inhibition at 10 µM as the criteria for defining a compound as a hit. We have been able to test 34 of these 46 compounds in a dose-response curve follow-up assay where we observed a 97% hit confirmation rate (33 out of 34 compounds confirmed). Many compounds exerted $IC_{50}$ values for inhibiting aggresome formation far and above the values for their indicated targets such as ELN476182, a 5HT1B antagonist, as well as Wortmannin, a PI3-kinase inhibitor. Thus, the exact mechanism by which many of the hits identified in this study are functioning, is not known. There were a number of compounds, such as ELN476235, ELN476311, ELN476491, ELN476767, ELN476780, ELN476809, and ELN477044, that exhibited IC50 values <0.078 µM. These compounds will be retested using a lower starting concentration in order to produce a complete dose-response curve. In terms of charactering cytotoxicity, compounds were given a low rating if the cell count was >75% of control levels, a medium rating if the cell count was between 50 and 75% of control wells, and a high rating if the cell count was less than 50% of control levels.

TABLE 3

| ELN | Class | TC50 | Parkin IC50 (uM) | Parkin Hill | CFTR IC50 | CFTR Hill | NRDP IC50 | NRDP Hill |
|---|---|---|---|---|---|---|---|---|
| 634 | Potent, cell-permeable, IP3-independent intracellular calcium releaser | | ND | ND | | | | |
| 17957 | Endothelial nitric oxide synthase inhibitor | 4.7 | 0.68 | 0.34 | 8.318 | 0.511 | 1.428 | 1.379 |
| 18065 | DNA topoisomerase II inhibitor | >10 | 2.12 | 0.54 | 0.849 | 3.147 | 0.689 | 1.476 |
| 27261 | Selective inhibitor of DNA synthesis | >10 | 1.93 | 1.32 | 3.148 | 1.17 | 2.50 | 0.29 |
| 29018 | DNA crosslinker; induces apoptosis | >10 | 7.25 | 1.02 | >10 | 0.312 | 32% @ 10 | 0.945 |
| 29019 | Thymidylate synthetase inhibitor; leads to accumulation of cells in S phase | >10 | 9.00 | 2.39 | >10 | 15 | 1.6 | 1.8 |
| 47510 | Ca2+ ionophore used to potentiate responses to NMDA, but not quisqualate glutamate receptors | 0.898 | 7.39 | 1.62 | >10 | 2.9 | 0.963 | 3.38 |
| 47586 | Selective PDGF tyrosine kinase receptor inhibitor | >10 | 0.371 | 0.215 | >10 | -3.1 | 0.6 | 4.8 |
| 475312 | Disrupts Microtubules | <0.078 | 1.07 | 2.69 | >10 | | >10 | |
| 476182 | 5HT1B antagonist | 6.8 | 8.48 | 1.28 | >10 | | 5.1 | 1.6 |
| 476198 | Inhibitor of Mg2+ and Na+/K+−ATPase; isolated from the leaves and stems of Macleaya cordata and microcarpa | 1.6 | 1.06 | 2.12 | 0.871 | 2.60 | 2.78 | 0.57 |
| 476201 | DNA methyltransferase inhibitor | >10 | 5.36 | 0.64 | >10 | | 5.814 | 1.1 |
| 476227 | Antineoplastic | >10 | 8.05 | 1.10 | >10 | | 5.8 | 0.50 |
| 476235 | DNA topoisomerase II inhibitor | >10 | <0.078 | ND | >10 | | >10 | |
| 476253 | Inhibits cytokine induced IkB (Inhibitor of NFkB) phosphorylation | 8.1 | 9.59 | 4.22 | >10 | | >10 | |

TABLE 3-continued

| ELN | Class | TC50 | Parkin IC50 (uM) | Parkin Hill | CFTR IC50 | CFTR Hill | NRDP IC50 | NRDP Hill |
|---|---|---|---|---|---|---|---|---|
| 476282 | Cdk1 inhibitor | >10 | 0.33 | 1.68 | 3.8 | 14.20 | 0.33 | 1.20 |
| 476301 | PP2A inhibitor | 6.5 | 6.86 | 1.34 | 6.159 | 2.40 | 4.02 | 1.60 |
| 476304 | pp1 and pp2A inhibitor | 1.6 | 2.46 | 1.20 | 5.545 | 4.228 | 3.90 | 1.70 |
| 476309 | chymotrypsin inhibitor | 10 | 4.12 | 1.60 | 3.876 | 1.53 | 0.26 | 1.23 |
| 476311 | Blocks tubulin polymerization | <0.078 | <0.078 | ND | >10 | | >10 | |
| 476313 | Sodium-potassium pump inhibitor | >10 | 1.08 | 0.82 | 3.527 | 1.43 | 1.49 | 1.38 |
| 476320 | Protein kinase C-alpha (PKC-alpha) inhibitor | 2.7 | 2.39 | 1.38 | >10 | 0.8 | <0.078 | 0.86 |
| 476325 | Selective blocker of apamin-sensitive K+ channels | 6.7 | 6.27 | 12.04 | >10 | | 1.76 | 4.20 |
| 476421 | Selective, irreversible Cdc25 dual specificity phosphatase inhibitor. | 4.4 | >10 | ND | >10 | | >10 | |
| 476469 | Antineoplastic; forms DNA intrastrand crosslinks by bifunctional alkylation in 5'-GGC sequences | >10 | 6.06 | 1.49 | >10 | | >10 | |
| 476478 | Nicotinic acetylcholine receptor antagonist; selectively inhibits alpha-bungarotoxin sensitive receptors that contain the alpha7 subunit | >10 | 9.90 | 1.38 | >10 | | 5.76 | 1.80 |
| 476489 | Irreversible peroxisome proliferator-activated receptor-gamma (PPAR-gamma) inhibitor | >10 | 9.59 | 0.64 | >10 | | >10 | |
| 476491 | DNA synthesis inhibitor | 6.53 | <0.078 | 3.13 | 1.582 | 8.178 | 1.5 | 9.5 |
| 476493 | Casein Kinase II inhibitor | >10 | >10 | | >10 | | >10 | |
| 476516 | cholinergic | | ND | ND | | | | |
| 476535 | Nitric oxide donor; activator of rat lung soluble guanylyl cyclase | | ND | ND | | | | |
| 476545 | CDK Inhibitor (phosphorylation) | >10 | 7.56 | 8.86 | >10 | | 7.8 | 2.10 |
| 476574 | PKC and CaM kinase III inhibitor | >10 | 2.83 | 1.40 | >10 | | 6.1 | 4.00 |
| 476577 | P2Y receptor antagonist; most potent antagonist for ATP-activated channels | >10 | 45% @ 10 | ND | >10 | | 9.9 | 1.1 |
| 476614 | Tyrosine kinase nerve growth factor receptor (TrkA) inhibitor; inhibits 140 trk protooncogene and HER-2 | 9.54 | 4.10 | 1.30 | >10 | | 2.06 | 2.25 |
| 476646 | Potent and specific phosphatidylinositol 3-kinase (P13-K) inhibitor | 1.9 | 0.75 | 1.76 | >10 | | >10 | |
| 476673 | Gs-alpha antagonist | | ND | ND | | | | |
| 476767 | inhibitor of microtubule assembly | <0.078 | <0.078 | ND | >10 | | >10 | |
| 476780 | inhibits tubulin | <0.078 | <0.156 | ND | >10 | | >10 | |
| 476809 | DNA metabolism | >10 | <0.078 | 0.71 | >10 | | 0.156 | |
| 477017 | Apoptosis Inducer | | ND | ND | | | | |
| 477044 | Blocks movement of the H5 and H6 transmembrane domains of Na+–K+ ATPases | 6.4 | <0.078 | ND | 0.226 | 1.96 | <0.078 | |
| 477056 | chymotrypsin inhibitor | >10 | 9.25 | 2.03 | >10 | | 5.47 | 2.62 |
| 477062 | Inhibitor of Microtubule Assembly | <0.078 | <0.078 | −6.76 | >10 | | >10 | |
| 477063 | Inhibitor of Microtubule Assembly | <0.078 | <0.078 | ND | >10 | | >10 | |

All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

The invention claimed is:

1. A method for identifying a Parkin modulating candidate compound for treatment of Parkinson's Disease comprising:
   (a) exposing a mammalian cell expressing exogenous Parkin to a test agent, wherein the cell does not express an exogenous mammalian protein other than Parkin;
   (b) comparing proteasome function in the cell and proteasome function characteristic of a corresponding mammalian cell expressing Parkin but not exposed to the test agent;
   wherein an increased level of proteasome function in the cell exposed to the test agent indicates the agent is a candidate compound for treatment of Parkinson's Disease;
   (c) exposing a mammalian cell expressing an exogenous mammalian protein other than Parkin to the candidate compound, wherein the cell does not express exogenous Parkin; and
   (d) comparing proteasome function in the cell in (c) and proteasome function characteristic of a cell expressing the exogenous mammalian protein but not exposed to the candidate compound;
   wherein absence of an increased level of proteasome function in cells expressing the exogenous mammalian protein other than Parkin indicates the candidate compound is a Parkin modulating candidate compound for treatment of Parkinson's Disease.

2. The method of claim 1 wherein the mammalian cells express a green fluorescent protein with a degradation signal (GFPu) and proteasome function is measured by measuring the amount of GFPu in the cells.

3. The method of claim 2 wherein the amount of GFPu in the cells is determined by measuring GFPu fluorescence.

4. The method of claim 1 wherein the cells are HEK293, SHSY-5Y, COS or CHO cells.

5. The method of claim 1 wherein the cells in (a) are cells transiently transfected with an expression vector encoding Parkin.

6. The method of claim 5 wherein after the transfection is initiated the cells are incubated 2-5 hours prior to addition of the test agent.

7. The method of claim 6 wherein proteasome function is measured about 45 hours after addition of the test agent.

8. The method of claim 5 wherein the cells are plated at a density of about 250-500 cells per $mm^2$.

9. The method of claim 8 wherein 8,000-16,000 cells per well are plated in wells having a surface area of about 32.15 $mm^2$.

10. The method of claim 1 wherein the Parkin in (a) is a Parkin mutant for which heterozygosity is correlated to development of PD.

11. The method of claim 1 wherein the exogenous mammalian protein is Huntingtin, NRDP1, SOD1, Rhodopsin, connexin 43, $Ub^{+1}$, presenilin, or Cystic Fibrosis Transmembrane Conductance Regulator (CFTR).

12. The method of claim 1 further comprising an in vitro activity assay comprising
   (i) measuring the E3 ligase activity of Parkin protein in the presence of the test agent or candidate compound; and
   (ii) comparing the E3 ligase activity of Parkin protein in the presence of the test agent or candidate compound with E3 activity of Parkin protein in the absence of the agent or compound.

13. The method of claim 12 in which the E3 ligase activity of purified Parkin protein is assayed.

14. The method of claim 1 further comprising an in vitro binding assay comprising:
   (i) contacting the test agent or candidate compound with purified Parkin protein; and,
   (ii) detecting the binding, if any, between the agent or compound and the Parkin protein.

15. A high-throughput screening method comprising assaying at least 25 test agents in parallel according to the method of claim 1.

16. The method of claim 15 carried out in 96-well cell culture plates.

17. The method of claim 15 comprising:
   (a) exposing a plurality of aliquots of mammalian cells expressing exogenous Parkin to test agents;
   (b) comparing proteasome function of cells in each aliquot with proteasome function characteristic of corresponding mammalian cells expressing Parkin but not exposed to any of said test agents;
   wherein an increased level of proteasome function in cells exposed to a test agent compared to cells not exposed to any test agent indicates the test agent is a candidate compound for treatment of Parkinson's Disease.

18. The method of claim 15 wherein the aliquots of mammalian cells expressing exogenous Parkin are transfected with a Parkin-encoding polynucleotide 2-4 hours prior to exposure to test agents and proteasome function is measured in the cells after 40-50 hours of exposure to the test agents.

19. The method of claim 1, wherein the exogenous Parkin is wild-type Parkin.

20. The method of claim 1, wherein the test agent has a molecular weight less than 1000.

* * * * *

UNITED STATES PATENT AND TRADEMARK OFFICE
CERTIFICATE OF CORRECTION

| | | |
|---|---|---|
| PATENT NO. | : 8,017,348 B1 | Page 1 of 1 |
| APPLICATION NO. | : 12/177100 | |
| DATED | : September 13, 2011 | |
| INVENTOR(S) | : Jennifer A. Johnston | |

It is certified that error appears in the above-identified patent and that said Letters Patent is hereby corrected as shown below:

Column 1, Line 8: delete "and", and after "2006" insert --, which claims the benefit of U.S. provisional application No. 60/749,964, filed Dec. 12, 2005.--

Column 1, Line 9: before "claims" insert --This application also--

Signed and Sealed this
First Day of November, 2011

David J. Kappos
*Director of the United States Patent and Trademark Office*

SEQUENCE LISTING

```
<160> NUMBER OF SEQ ID NOS: 11

<210> SEQ ID NO 1
<211> LENGTH: 1398
<212> TYPE: DNA
<213> ORGANISM: Homo sapiens

<400> SEQUENCE: 1
atgatagtgt tgtcaggtt caactccagc catggtttcc cagtggaggt cgattctgac      60
accagcatct tccagctcaa ggaggtggtt gctaagcgac agggggttcc ggctgaccag    120
ttgcgtgtga ttttcgcagg gaaggagctg aggaatgact ggactgtgca gaattgtgac    180
ctggatcagc agagcattgt tcacattgtg cagagaccgg ggagaaaagg tcaagaaatg    240
aatgcaactg gaggcgacga ccccagaaac gcggcgggag gctgtgagcg ggagcccag    300 agcttgactc gggtggacct cagcagctca gtcctcccag gagactctgt ggggctggct    360
gtcattctgc acactgacag caggaaggac tcaccaccag ctggaagtcc agcaggtaga    420
tcaatctaca acagctttta tgtgtattgc aaaggcccct gtcaaagagt gcagccggga    480
aaactcaggg tacagtgcag cacctgcagg caggcaacgc tcaccttgac ccagggtcca    540
tcttgctggg atgatgtttt aattccaaac cggatgagtg gtgaatgcca atccccacac    600
tgccctggga ctagtgcaga attttctctt aaatgtggag cacaccccac ctctgacaag    660
gaaacaccag tagctttgca cctgatcgca acaaatagtc ggaacatcac ttgcattacg    720
tgcacagacg tcaggagccc cgtcctggtt ttccagtgca actcccgcca cgtgatttgc    780
ttagactgtt tccacttata ctgtgtgaca agactcaatg atcggcagtt tgttcacgac    840
cctcaacttg gctactccct gccttgtgtg gctggctgtc ccaactcctt gattaaagag    900
ctccatcact tcaggattct gggagaagag cagtacaacc ggtaccagca gtatggtgca    960
gaggagtgtg tcctgcagat gggggggcgtg ttatgccccc gccctggctg tggagcgggg   1020
ctgctgccgg agcctgacca gaggaaagtc acctgcgaag ggggcaatgg cctgggctgt   1080 gggttttgcct tctgccggga atgtaaagaa gcgtaccatg aaggggagtg cagtgccgta   1140
tttgaagcct caggaacaac tactcaggcc tacagagtcg atgaaagagc cgccgagcag   1200
gctcgttggg aagcagcctc caaagaaacc atcaagaaaa ccaccaagcc ctgtccccgc   1260
tgccatgtac cagtggaaaa aaatggaggc tgcatgcaca tgaagtgtcc gcagccccag   1320
tgcaggctcg agtggtgctg gaactgtggc tgcgagtgga accgcgtctg catgggggac   1380
cactggttcg acgtgtag                                                 1398

<210> SEQ ID NO 2
<211> LENGTH: 465
<212> TYPE: PRT
<213> ORGANISM: Homo sapiens

<400> SEQUENCE: 2

Met Ile Val Phe Val Arg Phe Asn Ser Ser His Gly Phe Pro Val Glu
 1               5                  10                  15
```

```
Val Asp Ser Asp Thr Ser Ile Phe Gln Leu Lys Glu Val Ala Lys
         20                  25                  30

Arg Gln Gly Val Pro Ala Asp Gln Leu Arg Val Ile Phe Ala Gly Lys
             35                  40                  45

Glu Leu Arg Asn Asp Trp Thr Val Gln Asn Cys Asp Leu Asp Gln Gln
 50                  55                  60

Ser Ile Val His Ile Val Gln Arg Pro Trp Arg Lys Gly Gln Glu Met
 65                  70                  75                  80

Asn Ala Thr Gly Gly Asp Asp Pro Arg Asn Ala Ala Gly Gly Cys Glu
             85                  90                  95

Arg Glu Pro Gln Ser Leu Thr Arg Val Asp Leu Ser Ser Val Leu
             100                 105                 110

Pro Gly Asp Ser Val Gly Leu Ala Val Ile Leu His Thr Asp Ser Arg
             115                 120                 125

Lys Asp Ser Pro Pro Ala Gly Ser Pro Ala Gly Arg Ser Ile Tyr Asn
 130                 135                 140

Ser Phe Tyr Val Tyr Cys Lys Gly Pro Cys Gln Arg Val Gln Pro Gly
 145                 150                 155                 160

Lys Leu Arg Val Gln Cys Ser Thr Cys Arg Gln Ala Thr Leu Thr Leu
             165                 170                 175

Thr Gln Gly Pro Ser Cys Trp Asp Asp Val Leu Ile Pro Asn Arg Met
             180                 185                 190

Ser Gly Glu Cys Gln Ser Pro His Cys Pro Gly Thr Ser Ala Glu Phe
             195                 200                 205

Phe Phe Lys Cys Gly Ala His Pro Thr Ser Asp Lys Glu Thr Pro Val
 210                 215                 220

Ala Leu His Leu Ile Ala Thr Asn Ser Arg Asn Ile Thr Cys Ile Thr
 225                 230                 235                 240

Cys Thr Asp Val Arg Ser Pro Val Leu Val Phe Gln Cys Asn Ser Arg
             245                 250                 255

His Val Ile Cys Leu Asp Cys Phe His Leu Tyr Cys Val Thr Arg Leu
             260                 265                 270

Asn Asp Arg Gln Phe Val His Asp Pro Gln Leu Gly Tyr Ser Leu Pro
             275                 280                 285

Cys Val Ala Gly Cys Pro Asn Ser Leu Ile Lys Glu Leu His His Phe
 290                 295                 300

Arg Ile Leu Gly Glu Glu Gln Tyr Asn Arg Tyr Gln Gln Tyr Gly Ala
 305                 310                 315                 320

Glu Glu Cys Val Leu Gln Met Gly Gly Val Leu Cys Pro Arg Pro Gly
             325                 330                 335

Cys Gly Ala Gly Leu Leu Pro Glu Pro Asp Gln Arg Lys Val Thr Cys
             340                 345                 350

Glu Gly Gly Asn Gly Leu Gly Cys Gly Phe Ala Phe Cys Arg Glu Cys
             355                 360                 365

Lys Glu Ala Tyr His Glu Gly Glu Cys Ser Ala Val Phe Glu Ala Ser
 370                 375                 380

Gly Thr Thr Thr Gln Ala Tyr Arg Val Asp Glu Arg Ala Ala Glu Gln
 385                 390                 395                 400

Ala Arg Trp Glu Ala Ala Ser Lys Glu Thr Ile Lys Lys Thr Thr Lys
             405                 410                 415

Pro Cys Pro Arg Cys His Val Pro Val Glu Lys Asn Gly Gly Cys Met
 420                 425                 430

His Met Lys Cys Pro Gln Pro Gln Cys Arg Leu Glu Trp Cys Trp Asn
```

```
                435                 440                 445
        Cys Gly Cys Glu Trp Asn Arg Val Cys Met Gly Asp His Trp Phe Asp
            450                 455                 460

Val
        465
```

```
<210> SEQ ID NO 3
<211> LENGTH: 1395
<212> TYPE: DNA
<213> ORGANISM: Mus sp.

<400> SEQUENCE: 3
atgatagtgt tgtcaggtt caactccagc tatggcttcc cagtggaggt cgattctgac      60
accagcatct tgcagctcaa ggaagtggtt gctaagcgac aggggttcc agctgaccag     120 ctgcgtgtga ttttgccgg aaggagctt ccgaatcacc tgacggttca aaactgtgac     180
ctggaacaac agagtattgt acacatagta cagagaccac ggaggagaag tcatgaaaca     240
aatgcatctg gagggacga accccagagc acctcagagg gctccatatg ggagtccagg     300
agcttgacac gagtggacct gagcagccat accctgccgg tggactctgt ggggctggcg     360
gtcattctgg acacagacag taagagggat tcagaagcag ccagaggtcc agttaaaccc     420
acctacaaca gcttttcat ctactgcaaa ggccctgcc acaaggtcca gcctggaaag     480
ctccgagttc agtgtggcac ctgcaaacaa gcaaccctca ccttggccca gggcccatct     540
tgctgggacg atgtcttaat tccaaaccgg atgagtggtg agtgccagtc tccagactgc     600
cctggaacca gagctgaatt tttctttaaa tgtggagcac acccaacctc agacaaggac     660
acgtcggtag ctttgaacct gatcaccagc aacaggcgca gcatcccttg catagcgtgc     720
acagatgtca ggagccctgt cctggtcttc cagtgtaacc accgtcacgt gatctgtttg     780
gactgtttcc acttgtattg tgtcacaaga ctcaacgatc ggcagtttgt ccacgatgct     840
caacttggct actccctgcc gtgtgtagct ggctgtccca actccctgat taaagagctc     900
catcacttca ggatccttgg agaagagcag tacactaggt accagcagta tggggccgag     960
gaatgcgtgc tgcaaatggg aggtgtgctg tgccccgtc ctggctgtgg agctggactg    1020
ctacctgaac agggccagag gaaagtcacc tgcgaagggg caacggcct gggctgcggg    1080 tttgttttct gccgggactg taaggaagca taccatgaag gggattgcga ctcactgctc    1140
gaaccctcag gagccacttc tcaggcctac agggtggaca aaagagccgc tgagcaagct    1200
cgctgggagg aggcctccaa ggaaaccatc aagaagacca ccaagccttg tcctcgctgc    1260
aacgtgccaa ttgaaaaaaa cggaggatgt atgcacatga agtgtcctca gccccagtgc    1320
aagctggagt ggtgctggaa ctgtggctgt gagtggaacc gagcctgcat gggagatcac    1380
tggtttgacg tgtag                                                   1395
```

```
<210> SEQ ID NO 4
<211> LENGTH: 315
<212> TYPE: PRT
<213> ORGANISM: Mus sp.

<400> SEQUENCE: 4

Met Val Val Arg Asn Ser Ser Tyr Gly Val Val Asp Ser Asp Thr Ser
1               5                   10                  15

Lys Val Val Ala Lys Arg Gly Val Ala Asp Arg Val Ala Gly Lys Asn
            20                  25                  30

His Thr Val Asn Cys Asp Ser Val His Val Arg Arg Arg Ser His
        35                  40                  45
```

```
Thr Asn Ala Ser Gly Gly Asp Ser Thr Ser Gly Ser Trp Arg Ser
     50                  55                  60
Thr Arg Val Asp Ser Ser His Thr Val Asp Ser Val Gly Ala Val Asp
 65              70                  75                  80
Thr Asp Ser Lys Arg Asp Ser Ala Ala Arg Gly Val Lys Thr Tyr Asn
             85                  90                  95
Ser Tyr Cys Lys Gly Cys His Lys Val Gly Lys Arg Val Cys Gly Thr
            100                 105                 110
Cys Lys Ala Thr Thr Ala Gly Ser Cys Trp Asp Val Asn Arg Met
        115                 120                 125
Ser Gly Cys Ser Asp Cys Gly Thr Arg Ala Lys Cys Gly Ala His Thr
130                 135                 140
Ser Asp Lys Asp Thr Ser Val Ala Asn Thr Ser Asn Arg Arg Ser Cys
145                 150                 155                 160
Ala Cys Thr Asp Val Arg Ser Val Val Cys Asn His Arg His Val Cys
                165                 170                 175
Asp Cys His Tyr Cys Val Thr Arg Asn Asp Arg Val His Asp Ala Gly
            180                 185                 190
Tyr Ser Cys Val Ala Gly Cys Asn Ser Lys His His Arg Gly Tyr Thr
        195                 200                 205
Arg Tyr Tyr Gly Ala Cys Val Met Gly Gly Val Cys Arg Gly Cys Gly
210                 215                 220
Ala Gly Gly Arg Lys Val Thr Cys Gly Gly Asn Gly Gly Cys Gly Val
225                 230                 235                 240
Cys Arg Asp Cys Lys Ala Tyr His Gly Asp Cys Asp Ser Ser Gly Ala
                245                 250                 255
Thr Ser Ala Tyr Arg Val Asp Lys Arg Ala Ala Arg Trp Ala Ser
            260                 265                 270
Lys Thr Lys Lys Thr Thr Lys Cys Arg Cys Asn Val Lys Asn Gly Gly
        275                 280                 285
Cys Met His Met Lys Cys Lys Trp Cys Trp Asn Cys Gly Cys Trp
290                 295                 300
Asn Arg Ala Cys Met Gly Asp His Trp Asp Val
305                 310                 315
```

<210> SEQ ID NO 5
<211> LENGTH: 1566
<212> TYPE: DNA
<213> ORGANISM: Artificial
<220> FEATURE:
<223> OTHER INFORMATION: Full length human Parkin fused to histidine tag
<220> FEATURE:
<221> NAME/KEY: misc_feature
<222> LOCATION: (14)..(29)
<223> OTHER INFORMATION: His sequence
<220> FEATURE:
<221> NAME/KEY: misc_feature
<222> LOCATION: (157)..(168)
<223> OTHER INFORMATION: Kozac sequence

<400> SEQUENCE: 5

```
atatacatat gcaccatcat catcatcatt tcttctggtc tggtgccacg cggttctggt    60
atgaaagaaa ccgctgctgc taaattcgaa cgccagcaca tggacagccc agatctgggt   120
accgacgacg acgacaaggc catggctgat atcggatccg ccgccaccat gatagtgttt   180
gtcaggttca actccagcca tggtttccca gtggaggtcg attctgacac cagcatcttc   240
cagctcaagg aggtggttgc taagcgacag ggggttccgg ctgaccagtt gcgtgtgatt   300
```

```
ttcgcaggga aggagctgag gaatgactgg actgtgcaga attgtgacct ggatcagcag      360
agcattgttc acattgtgca gagaccgtgg agaaaaggtc aagaaatgaa tgcaactgga      420
ggcgacgacc ccagaaacgc ggcgggaggc tgtgagcggg agccccagag cttgactcgg      480
gtggacctca gcagctcagt cctcccagga gactctgtgg ggctggctgt cattctgcac      540
actgacagca ggaaggactc accaccagct ggaagtccag caggtagatc aatctacaac      600
agcttttatg tgtattgcaa aggccctgt caaagagtgc agcccgggaaa actcagggta      660
cagtgcagca cctgcaggca ggcaacgctc accttgaccc agggtccatc ttgctgggat      720
gatgttttaa ttccaaaccg gatgagtggt gaatgccaat ccccacactg ccctgggact      780
agtgcagaat ttttctttaa atgtggagca caccccacct ctgacaagga aacaccagta      840
gctttgcacc tgatcgcaac aaatagtcgg aacatcactt gcattacgtg cacagacgtc      900
aggagccccg tcctggtttt ccagtgcaac tcccgccacg tgatttgctt agactgtttc      960
cacttatact gtgtgacaag actcaatgat cggcagtttg ttcacgaccc tcaacttggc     1020
tactccctgc cttgtgtggc tggctgtccc aactccttga ttaaagagct ccatcacttc     1080
aggattctgg gagaagagca gtacaaccgg taccagcagt atggtgcaga ggagtgtgtc     1140
ctgcagatgg ggggcgtgtt atgccccgc cctggctgtg gagcggggct gctgccggag     1200
cctgaccaga ggaaagtcac ctgcgaaggg ggcaatggcc tgggctgtgg gtttgccttc     1260
tgccgggaat gtaagaagc gtaccatgaa ggggagtgca gtgccgtatt tgaagcctca     1320
ggaacaacta ctcaggccta cagagtcgat gaaagagccg ccgagcaggc tcgttgggaa     1380
gcagcctcca agaaaccat caagaaaacc accaagccct gtccccgctg ccatgtacca     1440
gtggaaaaaa atggaggctg catgcacatg aagtgtccgc agccccagtg caggctcgag     1500
tggtgctgga actgtgctg cgagtggaac cgcgtctgca tggggaccag ctggttcgac     1560
gtgtag                                                                1566

<210> SEQ ID NO 6
<211> LENGTH: 720
<212> TYPE: DNA
<213> ORGANISM: Artificial
<220> FEATURE:
<223> OTHER INFORMATION: Green fluorescent protein

<400> SEQUENCE: 6
atggtgagca agggcgagga gctgttcacc ggggtggtgc ccatcctggt cgagctggac       60
ggcgacgtaa acggccacaa gttcagcgtg tccggcgagg gcgagggcga tgccacctac      120
ggcaagctga ccctgaagtt catctgcacc accggcaagc tgcccgtgcc ctggcccacc      180
ctcgtgacca ccctgaccta cggcgtgcag tgcttcagcc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagtag      720

<210> SEQ ID NO 7
```

```
<211> LENGTH: 239
<212> TYPE: PRT
<213> ORGANISM: Artificial
<220> FEATURE:
<223> OTHER INFORMATION: Green fluorescent protein

<400> SEQUENCE: 7
```

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

```
<210> SEQ ID NO 8
<211> LENGTH: 60
<212> TYPE: DNA
<213> ORGANISM: Artificial
<220> FEATURE:
<223> OTHER INFORMATION: Degradation signal (Degron)

<400> SEQUENCE: 8
```
gagatatcgc ttgcaaagaa ctggttctct tccttgagtc acttcgtaat tcacttgtag    60

```
<210> SEQ ID NO 9
<211> LENGTH: 19
<212> TYPE: PRT
<213> ORGANISM: Artificial
<220> FEATURE:
<223> OTHER INFORMATION: Degradation signal (Degron)

<400> SEQUENCE: 9
```

Glu Ile Ser Leu Ala Lys Asn Trp Phe Ser Ser Leu Ser His Phe Val
1               5                   10                  15

Ile His Leu

-continued

```
<210> SEQ ID NO 10
<211> LENGTH: 1480
<212> TYPE: PRT
<213> ORGANISM: Artificial
<220> FEATURE:
<223> OTHER INFORMATION: CFTR protein

<400> SEQUENCE: 10
```

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu

```
              370                 375                 380
Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                    405                 410                 415

Asn Asn Arg Lys Thr Ser Asn Gly Asp Asp Ser Leu Phe Phe Ser Asn
                420                 425                 430

Phe Ser Leu Leu Gly Thr Pro Val Leu Lys Asp Ile Asn Phe Lys Ile
                435                 440                 445

Glu Arg Gly Gln Leu Leu Ala Val Ala Gly Ser Thr Gly Ala Gly Lys
450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
                500                 505                 510

Asp Glu Tyr Arg Tyr Arg Ser Val Ile Lys Ala Cys Gln Leu Glu Glu
                515                 520                 525

Asp Ile Ser Lys Phe Ala Glu Lys Asp Asn Ile Val Leu Gly Glu Gly
                530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
                580                 585                 590

Lys Leu Met Ala Asn Lys Thr Arg Ile Leu Val Thr Ser Lys Met Glu
                595                 600                 605

His Leu Lys Lys Ala Asp Lys Ile Leu Ile Leu Asn Glu Gly Ser Ser
                610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
                660                 665                 670

Gly Asp Ala Pro Val Ser Trp Thr Glu Thr Lys Lys Gln Ser Phe Lys
                675                 680                 685

Gln Thr Gly Glu Phe Gly Glu Lys Arg Lys Asn Ser Ile Leu Asn Pro
690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
                740                 745                 750

Ser Val Ile Ser Thr Gly Pro Thr Leu Gln Ala Arg Arg Arg Gln Ser
                755                 760                 765

Val Leu Asn Leu Met Thr His Ser Val Asn Gln Gly Gln Asn Ile His
                770                 775                 780

Arg Lys Thr Thr Ala Ser Thr Arg Lys Val Ser Leu Ala Pro Gln Ala
785                 790                 795                 800
```

-continued

Asn Leu Thr Glu Leu Asp Ile Tyr Ser Arg Arg Leu Ser Gln Glu Thr
            805                 810                 815

Gly Leu Glu Ile Ser Glu Glu Ile Asn Glu Glu Asp Leu Lys Glu Cys
            820                 825                 830

Leu Phe Asp Asp Met Glu Ser Ile Pro Ala Val Thr Thr Trp Asn Thr
            835                 840                 845

Tyr Leu Arg Tyr Ile Thr Val His Lys Ser Leu Ile Phe Val Leu Ile
            850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
            885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
            915                 920                 925

Met Gly Phe Phe Arg Gly Leu Pro Leu Val His Thr Leu Ile Thr Val
            930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
            965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
            995                 1000                1005

Ala Val Leu Gln Pro Tyr Ile Phe Val Ala Thr Val Pro Val Ile
    1010                1015                1020

Val Ala Phe Ile Met Leu Arg Ala Tyr Phe Leu Gln Thr Ser Gln
    1025                1030                1035

Gln Leu Lys Gln Leu Glu Ser Glu Gly Arg Ser Pro Ile Phe Thr
    1040                1045                1050

His Leu Val Thr Ser Leu Lys Gly Leu Trp Thr Leu Arg Ala Phe
    1055                1060                1065

Gly Arg Gln Pro Tyr Phe Glu Thr Leu Phe His Lys Ala Leu Asn
    1070                1075                1080

Leu His Thr Ala Asn Trp Phe Leu Tyr Leu Ser Thr Leu Arg Trp
    1085                1090                1095

Phe Gln Met Arg Ile Glu Met Ile Phe Val Ile Phe Phe Ile Ala
    1100                1105                1110

Val Thr Phe Ile Ser Ile Leu Thr Thr Gly Glu Gly Glu Gly Arg
    1115                1120                1125

Val Gly Ile Ile Leu Thr Leu Ala Met Asn Ile Met Ser Thr Leu
    1130                1135                1140

Gln Trp Ala Val Asn Ser Ser Ile Asp Val Asp Ser Leu Met Arg
    1145                1150                1155

Ser Val Ser Arg Val Phe Lys Phe Ile Asp Met Pro Thr Glu Gly
    1160                1165                1170

Lys Pro Thr Lys Ser Thr Lys Pro Tyr Lys Asn Gly Gln Leu Ser
    1175                1180                1185

Lys Val Met Ile Ile Glu Asn Ser His Val Lys Lys Asp Asp Ile
    1190                1195                1200

Trp Pro Ser Gly Gly Gln Met Thr Val Lys Asp Leu Thr Ala Lys
    1205                1210                1215

| | | | | | | | | | | | |
|---|---|---|---|---|---|---|---|---|---|---|---|
| Tyr | Thr | Glu | Gly | Gly | Asn | Ala | Ile | Leu | Glu | Asn | Ile | Ser | Phe | Ser |
| | 1220 | | | | 1225 | | | | 1230 | | |

Tyr Thr Glu Gly Gly Asn Ala Ile Leu Glu Asn Ile Ser Phe Ser
    1220                1225                1230

Ile Ser Pro Gly Gln Arg Val Gly Leu Leu Gly Arg Thr Gly Ser
    1235                1240                1245

Gly Lys Ser Thr Leu Leu Ser Ala Phe Leu Arg Leu Leu Asn Thr
    1250                1255                1260

Glu Gly Glu Ile Gln Ile Asp Gly Val Ser Trp Asp Ser Ile Thr
    1265                1270                1275

Leu Gln Gln Trp Arg Lys Ala Phe Gly Val Ile Pro Gln Lys Val
    1280                1285                1290

Phe Ile Phe Ser Gly Thr Phe Arg Lys Asn Leu Asp Pro Tyr Glu
    1295                1300                1305

Gln Trp Ser Asp Gln Glu Ile Trp Lys Val Ala Asp Glu Val Gly
    1310                1315                1320

Leu Arg Ser Val Ile Glu Gln Phe Pro Gly Lys Leu Asp Phe Val
    1325                1330                1335

Leu Val Asp Gly Gly Cys Val Leu Ser His Gly His Lys Gln Leu
    1340                1345                1350

Met Cys Leu Ala Arg Ser Val Leu Ser Lys Ala Lys Ile Leu Leu
    1355                1360                1365

Leu Asp Glu Pro Ser Ala His Leu Asp Pro Val Thr Tyr Gln Ile
    1370                1375                1380

Ile Arg Arg Thr Leu Lys Gln Ala Phe Ala Asp Cys Thr Val Ile
    1385                1390                1395

Leu Cys Glu His Arg Ile Glu Ala Met Leu Glu Cys Gln Gln Phe
    1400                1405                1410

Leu Val Ile Glu Glu Asn Lys Val Arg Gln Tyr Asp Ser Ile Gln
    1415                1420                1425

Lys Leu Leu Asn Glu Arg Ser Leu Phe Arg Gln Ala Ile Ser Pro
    1430                1435                1440

Ser Asp Arg Val Lys Leu Phe Pro His Arg Asn Ser Ser Lys Cys
    1445                1450                1455

Lys Ser Lys Pro Gln Ile Ala Ala Leu Lys Glu Glu Thr Glu Glu
    1460                1465                1470

Glu Val Gln Asp Thr Arg Leu
    1475                1480

<210> SEQ ID NO 11
<211> LENGTH: 3142
<212> TYPE: PRT
<213> ORGANISM: Artificial
<220> FEATURE:
<223> OTHER INFORMATION: Huntingtin protein

<400> SEQUENCE: 11

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln
            20                  25                  30

Gln Gln Gln Gln Gln Gln Pro Pro Pro Pro Pro Pro Pro Pro
        35                  40                  45

Pro Gln Leu Pro Gln Pro Pro Pro Gln Ala Gln Pro Leu Leu Pro Gln
    50                  55                  60

Pro Gln Pro Pro Pro Pro Pro Pro Pro Pro Gly Pro Ala Val
65                  70                  75                  80

```
Ala Glu Glu Pro Leu His Arg Pro Lys Lys Glu Leu Ser Ala Thr Lys
             85                  90                  95

Lys Asp Arg Val Asn His Cys Leu Thr Ile Cys Glu Asn Ile Val Ala
        100                 105                 110

Gln Ser Val Arg Asn Ser Pro Glu Phe Gln Lys Leu Leu Gly Ile Ala
    115                 120                 125

Met Glu Leu Phe Leu Leu Cys Ser Asp Asp Ala Glu Ser Asp Val Arg
130                 135                 140

Met Val Ala Asp Glu Cys Leu Asn Lys Val Ile Lys Ala Leu Met Asp
145                 150                 155                 160

Ser Asn Leu Pro Arg Leu Gln Leu Glu Leu Tyr Lys Glu Ile Lys Lys
                165                 170                 175

Asn Gly Ala Pro Arg Ser Leu Arg Ala Ala Leu Trp Arg Phe Ala Glu
            180                 185                 190

Leu Ala His Leu Val Arg Pro Gln Lys Cys Arg Pro Tyr Leu Val Asn
        195                 200                 205

Leu Leu Pro Cys Leu Thr Arg Thr Ser Lys Arg Pro Glu Glu Ser Val
210                 215                 220

Gln Glu Thr Leu Ala Ala Ala Val Pro Lys Ile Met Ala Ser Phe Gly
225                 230                 235                 240

Asn Phe Ala Asn Asp Asn Glu Ile Lys Val Leu Leu Lys Ala Phe Ile
                245                 250                 255

Ala Asn Leu Lys Ser Ser Ser Pro Thr Ile Arg Arg Thr Ala Ala Gly
            260                 265                 270

Ser Ala Val Ser Ile Cys Gln His Ser Arg Arg Thr Gln Tyr Phe Tyr
        275                 280                 285

Ser Trp Leu Leu Asn Val Leu Leu Gly Leu Leu Val Pro Val Glu Asp
290                 295                 300

Glu His Ser Thr Leu Leu Ile Leu Gly Val Leu Leu Thr Leu Arg Tyr
305                 310                 315                 320

Leu Val Pro Leu Leu Gln Gln Val Lys Asp Thr Ser Leu Lys Gly
                325                 330                 335

Ser Phe Gly Val Thr Arg Lys Glu Met Glu Val Ser Pro Ser Ala Glu
            340                 345                 350

Gln Leu Val Gln Val Tyr Glu Leu Thr Leu His His Thr Gln His Gln
        355                 360                 365

Asp His Asn Val Val Thr Gly Ala Leu Glu Leu Leu Gln Gln Leu Phe
370                 375                 380

Arg Thr Pro Pro Pro Glu Leu Leu Gln Thr Leu Thr Ala Val Gly Gly
385                 390                 395                 400

Ile Gly Gln Leu Thr Ala Ala Lys Glu Glu Ser Gly Gly Arg Ser Arg
                405                 410                 415

Ser Gly Ser Ile Val Glu Leu Ile Ala Gly Gly Gly Ser Ser Cys Ser
            420                 425                 430

Pro Val Leu Ser Arg Lys Gln Lys Gly Lys Val Leu Leu Gly Glu Glu
        435                 440                 445

Glu Ala Leu Glu Asp Asp Ser Glu Ser Arg Ser Asp Val Ser Ser Ser
450                 455                 460

Ala Leu Thr Ala Ser Val Lys Asp Glu Ile Ser Gly Glu Leu Ala Ala
465                 470                 475                 480

Ser Ser Gly Val Ser Thr Pro Gly Ser Ala Gly His Asp Ile Ile Thr
                485                 490                 495

Glu Gln Pro Arg Ser Gln His Thr Leu Gln Ala Asp Ser Val Asp Leu
            500                 505                 510
```

```
Ala Ser Cys Asp Leu Thr Ser Ser Ala Thr Asp Gly Asp Glu Glu Asp
        515                 520                 525
Ile Leu Ser His Ser Ser Gln Val Ser Ala Val Pro Ser Asp Pro
        530                 535                 540
Ala Met Asp Leu Asn Asp Gly Thr Gln Ala Ser Ser Pro Ile Ser Asp
545                 550                 555                 560
Ser Ser Gln Thr Thr Thr Glu Gly Pro Asp Ser Ala Val Thr Pro Ser
                565                 570                 575
Asp Ser Ser Glu Ile Val Leu Asp Gly Thr Asp Asn Gln Tyr Leu Gly
            580                 585                 590
Leu Gln Ile Gly Gln Pro Gln Asp Glu Asp Glu Ala Thr Gly Ile
        595                 600                 605
Leu Pro Asp Glu Ala Ser Glu Ala Phe Arg Asn Ser Ser Met Ala Leu
        610                 615                 620
Gln Gln Ala His Leu Leu Lys Asn Met Ser His Cys Arg Gln Pro Ser
625                 630                 635                 640
Asp Ser Ser Val Asp Lys Phe Val Leu Arg Asp Glu Ala Thr Glu Pro
                645                 650                 655
Gly Asp Gln Glu Asn Lys Pro Cys Arg Ile Lys Gly Asp Ile Gly Gln
            660                 665                 670
Ser Thr Asp Asp Ser Ala Pro Leu Val His Cys Val Arg Leu Leu
        675                 680                 685
Ser Ala Ser Phe Leu Leu Thr Gly Gly Lys Asn Val Leu Val Pro Asp
        690                 695                 700
Arg Asp Val Arg Val Ser Val Lys Ala Leu Ala Leu Ser Cys Val Gly
705                 710                 715                 720
Ala Ala Val Ala Leu His Pro Glu Ser Phe Phe Ser Lys Leu Tyr Lys
                725                 730                 735
Val Pro Leu Asp Thr Thr Glu Tyr Pro Glu Glu Gln Tyr Val Ser Asp
            740                 745                 750
Ile Leu Asn Tyr Ile Asp His Gly Asp Pro Gln Val Arg Gly Ala Thr
        755                 760                 765
Ala Ile Leu Cys Gly Thr Leu Ile Cys Ser Ile Leu Ser Arg Ser Arg
        770                 775                 780
Phe His Val Gly Asp Trp Met Gly Thr Ile Arg Thr Leu Thr Gly Asn
785                 790                 795                 800
Thr Phe Ser Leu Ala Asp Cys Ile Pro Leu Leu Arg Lys Thr Leu Lys
                805                 810                 815
Asp Glu Ser Ser Val Thr Cys Lys Leu Ala Cys Thr Ala Val Arg Asn
            820                 825                 830
Cys Val Met Ser Leu Cys Ser Ser Ser Tyr Ser Glu Leu Gly Leu Gln
        835                 840                 845
Leu Ile Ile Asp Val Leu Thr Leu Arg Asn Ser Ser Tyr Trp Leu Val
        850                 855                 860
Arg Thr Glu Leu Leu Glu Thr Leu Ala Glu Ile Asp Phe Arg Leu Val
865                 870                 875                 880
Ser Phe Leu Glu Ala Lys Ala Glu Asn Leu His Arg Gly Ala His His
                885                 890                 895
Tyr Thr Gly Leu Leu Lys Leu Gln Glu Arg Val Leu Asn Asn Val Val
            900                 905                 910
Ile His Leu Leu Gly Asp Glu Asp Pro Arg Val Arg His Val Ala Ala
        915                 920                 925
Ala Ser Leu Ile Arg Leu Val Pro Lys Leu Phe Tyr Lys Cys Asp Gln
```

-continued

```
            930                 935                 940
Gly Gln Ala Asp Pro Val Val Ala Val Ala Arg Asp Gln Ser Ser Val
945                 950                 955                 960

Tyr Leu Lys Leu Leu Met His Glu Thr Gln Pro Pro Ser His Phe Ser
                965                 970                 975

Val Ser Thr Ile Thr Arg Ile Tyr Arg Gly Tyr Asn Leu Leu Pro Ser
                980                 985                 990

Ile Thr Asp Val Thr Met Glu Asn Asn Leu Ser Arg Val Ile Ala Ala
                995                1000                1005

Val Ser His Glu Leu Ile Thr Ser Thr Thr Arg Ala Leu Thr Phe
   1010                1015                1020

Gly Cys Cys Glu Ala Leu Cys Leu Leu Ser Thr Ala Phe Pro Val
   1025                1030                1035

Cys Ile Trp Ser Leu Gly Trp His Cys Gly Val Pro Pro Leu Ser
   1040                1045                1050

Ala Ser Asp Glu Ser Arg Lys Ser Cys Thr Val Gly Met Ala Thr
   1055                1060                1065

Met Ile Leu Thr Leu Leu Ser Ser Ala Trp Phe Pro Leu Asp Leu
   1070                1075                1080

Ser Ala His Gln Asp Ala Leu Ile Leu Ala Gly Asn Leu Leu Ala
   1085                1090                1095

Ala Ser Ala Pro Lys Ser Leu Arg Ser Ser Trp Ala Ser Glu Glu
   1100                1105                1110

Glu Ala Asn Pro Ala Ala Thr Lys Gln Glu Glu Val Trp Pro Ala
   1115                1120                1125

Leu Gly Asp Arg Ala Leu Val Pro Met Val Glu Gln Leu Phe Ser
   1130                1135                1140

His Leu Leu Lys Val Ile Asn Ile Cys Ala His Val Leu Asp Asp
   1145                1150                1155

Val Ala Pro Gly Pro Ala Ile Lys Ala Ala Leu Pro Ser Leu Thr
   1160                1165                1170

Asn Pro Pro Ser Leu Ser Pro Ile Arg Arg Lys Gly Lys Glu Lys
   1175                1180                1185

Glu Pro Gly Glu Gln Ala Ser Val Pro Leu Ser Pro Lys Lys Gly
   1190                1195                1200

Ser Glu Ala Ser Ala Ala Ser Arg Gln Ser Asp Thr Ser Gly Pro
   1205                1210                1215

Val Thr Thr Ser Lys Ser Ser Ser Leu Gly Ser Phe Tyr His Leu
   1220                1225                1230

Pro Ser Tyr Leu Lys Leu His Asp Val Leu Lys Ala Thr His Ala
   1235                1240                1245

Asn Tyr Lys Val Thr Leu Asp Leu Gln Asn Ser Thr Glu Lys Phe
   1250                1255                1260

Gly Gly Phe Leu Arg Ser Ala Leu Asp Val Leu Ser Gln Ile Leu
   1265                1270                1275

Glu Leu Ala Thr Leu Gln Asp Ile Gly Lys Cys Val Glu Glu Ile
   1280                1285                1290

Leu Gly Tyr Leu Lys Ser Cys Phe Ser Arg Glu Pro Met Met Ala
   1295                1300                1305

Thr Val Cys Val Gln Gln Leu Leu Lys Thr Leu Phe Gly Thr Asn
   1310                1315                1320

Leu Ala Ser Gln Phe Asp Gly Leu Ser Ser Asn Pro Ser Lys Ser
   1325                1330                1335
```

-continued

```
Gln Gly Arg Ala Gln Arg Leu Gly Ser Ser Val Arg Pro Gly
    1340                1345                1350

Leu Tyr His Tyr Cys Phe Met Ala Pro Tyr Thr His Phe Thr Gln
    1355                1360                1365

Ala Leu Ala Asp Ala Ser Leu Arg Asn Met Val Gln Ala Glu Gln
    1370                1375                1380

Glu Asn Asp Thr Ser Gly Trp Phe Asp Val Leu Gln Lys Val Ser
    1385                1390                1395

Thr Gln Leu Lys Thr Asn Leu Thr Ser Val Thr Lys Asn Arg Ala
    1400                1405                1410

Asp Lys Asn Ala Ile His Asn His Ile Arg Leu Phe Glu Pro Leu
    1415                1420                1425

Val Ile Lys Ala Leu Lys Gln Tyr Thr Thr Thr Thr Cys Val Gln
    1430                1435                1440

Leu Gln Lys Gln Val Leu Asp Leu Leu Ala Gln Leu Val Gln Leu
    1445                1450                1455

Arg Val Asn Tyr Cys Leu Leu Asp Ser Asp Gln Val Phe Ile Gly
    1460                1465                1470

Phe Val Leu Lys Gln Phe Glu Tyr Ile Glu Val Gly Gln Phe Arg
    1475                1480                1485

Glu Ser Glu Ala Ile Ile Pro Asn Ile Phe Phe Phe Leu Val Leu
    1490                1495                1500

Leu Ser Tyr Glu Arg Tyr His Ser Lys Gln Ile Ile Gly Ile Pro
    1505                1510                1515

Lys Ile Ile Gln Leu Cys Asp Gly Ile Met Ala Ser Gly Arg Lys
    1520                1525                1530

Ala Val Thr His Ala Ile Pro Ala Leu Gln Pro Ile Val His Asp
    1535                1540                1545

Leu Phe Val Leu Arg Gly Thr Asn Lys Ala Asp Ala Gly Lys Glu
    1550                1555                1560

Leu Glu Thr Gln Lys Glu Val Val Val Ser Met Leu Leu Arg Leu
    1565                1570                1575

Ile Gln Tyr His Gln Val Leu Glu Met Phe Ile Leu Val Leu Gln
    1580                1585                1590

Gln Cys His Lys Glu Asn Glu Asp Lys Trp Lys Arg Leu Ser Arg
    1595                1600                1605

Gln Ile Ala Asp Ile Ile Leu Pro Met Leu Ala Lys Gln Gln Met
    1610                1615                1620

His Ile Asp Ser His Glu Ala Leu Gly Val Leu Asn Thr Leu Phe
    1625                1630                1635

Glu Ile Leu Ala Pro Ser Ser Leu Arg Pro Val Asp Met Leu Leu
    1640                1645                1650

Arg Ser Met Phe Val Thr Pro Asn Thr Met Ala Ser Val Ser Thr
    1655                1660                1665

Val Gln Leu Trp Ile Ser Gly Ile Leu Ala Ile Leu Arg Val Leu
    1670                1675                1680

Ile Ser Gln Ser Thr Glu Asp Ile Val Leu Ser Arg Ile Gln Glu
    1685                1690                1695

Leu Ser Phe Ser Pro Tyr Leu Ile Ser Cys Thr Val Ile Asn Arg
    1700                1705                1710

Leu Arg Asp Gly Asp Ser Thr Ser Thr Leu Glu Glu His Ser Glu
    1715                1720                1725

Gly Lys Gln Ile Lys Asn Leu Pro Glu Glu Thr Phe Ser Arg Phe
    1730                1735                1740
```

```
Leu Leu Gln Leu Val Gly Ile Leu Leu Glu Asp Ile Val Thr Lys
    1745            1750                1755
Gln Leu Lys Val Glu Met Ser Glu Gln Gln His Thr Phe Tyr Cys
    1760            1765                1770
Gln Glu Leu Gly Thr Leu Leu Met Cys Leu Ile His Ile Phe Lys
    1775            1780                1785
Ser Gly Met Phe Arg Arg Ile Thr Ala Ala Thr Arg Leu Phe
    1790            1795                1800
Arg Ser Asp Gly Cys Gly Gly Ser Phe Tyr Thr Leu Asp Ser Leu
    1805            1810                1815
Asn Leu Arg Ala Arg Ser Met Ile Thr Thr His Pro Ala Leu Val
    1820            1825                1830
Leu Leu Trp Cys Gln Ile Leu Leu Leu Val Asn His Thr Asp Tyr
    1835            1840                1845
Arg Trp Trp Ala Glu Val Gln Gln Thr Pro Lys Arg His Ser Leu
    1850            1855                1860
Ser Ser Thr Lys Leu Leu Ser Pro Gln Met Ser Gly Glu Glu Glu
    1865            1870                1875
Asp Ser Asp Leu Ala Ala Lys Leu Gly Met Cys Asn Arg Glu Ile
    1880            1885                1890
Val Arg Arg Gly Ala Leu Ile Leu Phe Cys Asp Tyr Val Cys Gln
    1895            1900                1905
Asn Leu His Asp Ser Glu His Leu Thr Trp Leu Ile Val Asn His
    1910            1915                1920
Ile Gln Asp Leu Ile Ser Leu Ser His Glu Pro Pro Val Gln Asp
    1925            1930                1935
Phe Ile Ser Ala Val His Arg Asn Ser Ala Ala Ser Gly Leu Phe
    1940            1945                1950
Ile Gln Ala Ile Gln Ser Arg Cys Glu Asn Leu Ser Thr Pro Thr
    1955            1960                1965
Met Leu Lys Lys Thr Leu Gln Cys Leu Glu Gly Ile His Leu Ser
    1970            1975                1980
Gln Ser Gly Ala Val Leu Thr Leu Tyr Val Asp Arg Leu Leu Cys
    1985            1990                1995
Thr Pro Phe Arg Val Leu Ala Arg Met Val Asp Ile Leu Ala Cys
    2000            2005                2010
Arg Arg Val Glu Met Leu Leu Ala Ala Asn Leu Gln Ser Ser Met
    2015            2020                2025
Ala Gln Leu Pro Met Glu Glu Leu Asn Arg Ile Gln Glu Tyr Leu
    2030            2035                2040
Gln Ser Ser Gly Leu Ala Gln Arg His Gln Arg Leu Tyr Ser Leu
    2045            2050                2055
Leu Asp Arg Phe Arg Leu Ser Thr Met Gln Asp Ser Leu Ser Pro
    2060            2065                2070
Ser Pro Pro Val Ser Ser His Pro Leu Asp Gly Asp Gly His Val
    2075            2080                2085
Ser Leu Glu Thr Val Ser Pro Asp Lys Asp Trp Tyr Val His Leu
    2090            2095                2100
Val Lys Ser Gln Cys Trp Thr Arg Ser Asp Ser Ala Leu Leu Glu
    2105            2110                2115
Gly Ala Glu Leu Val Asn Arg Ile Pro Ala Glu Asp Met Asn Ala
    2120            2125                2130
Phe Met Met Asn Ser Glu Phe Asn Leu Ser Leu Leu Ala Pro Cys
```

2135                2140                  2145

Leu Ser Leu Gly Met Ser Glu Ile Ser Gly Gly Gln Lys Ser Ala
    2150                2155                2160

Leu Phe Glu Ala Ala Arg Glu Val Thr Leu Ala Arg Val Ser Gly
    2165                2170                2175

Thr Val Gln Gln Leu Pro Ala Val His His Val Phe Gln Pro Glu
    2180                2185                2190

Leu Pro Ala Glu Pro Ala Ala Tyr Trp Ser Lys Leu Asn Asp Leu
    2195                2200                2205

Phe Gly Asp Ala Ala Leu Tyr Gln Ser Leu Pro Thr Leu Ala Arg
    2210                2215                2220

Ala Leu Ala Gln Tyr Leu Val Val Ser Lys Leu Pro Ser His
    2225                2230                2235

Leu His Leu Pro Pro Glu Lys Glu Lys Asp Ile Val Lys Phe Val
    2240                2245                2250

Val Ala Thr Leu Glu Ala Leu Ser Trp His Leu Ile His Glu Gln
    2255                2260                2265

Ile Pro Leu Ser Leu Asp Leu Gln Ala Gly Leu Asp Cys Cys Cys
    2270                2275                2280

Leu Ala Leu Gln Leu Pro Gly Leu Trp Ser Val Val Ser Ser Thr
    2285                2290                2295

Glu Phe Val Thr His Ala Cys Ser Leu Ile Tyr Cys Val His Phe
    2300                2305                2310

Ile Leu Glu Ala Val Ala Val Gln Pro Gly Glu Gln Leu Leu Ser
    2315                2320                2325

Pro Glu Arg Arg Thr Asn Thr Pro Lys Ala Ile Ser Glu Glu Glu
    2330                2335                2340

Glu Glu Val Asp Pro Asn Thr Gln Asn Pro Lys Tyr Ile Thr Ala
    2345                2350                2355

Ala Cys Glu Met Val Ala Glu Met Val Glu Ser Leu Gln Ser Val
    2360                2365                2370

Leu Ala Leu Gly His Lys Arg Asn Ser Gly Val Pro Ala Phe Leu
    2375                2380                2385

Thr Pro Leu Leu Arg Asn Ile Ile Ile Ser Leu Ala Arg Leu Pro
    2390                2395                2400

Leu Val Asn Ser Tyr Thr Arg Val Pro Pro Leu Val Trp Lys Leu
    2405                2410                2415

Gly Trp Ser Pro Lys Pro Gly Gly Asp Phe Gly Thr Ala Phe Pro
    2420                2425                2430

Glu Ile Pro Val Glu Phe Leu Gln Glu Lys Glu Val Phe Lys Glu
    2435                2440                2445

Phe Ile Tyr Arg Ile Asn Thr Leu Gly Trp Thr Ser Arg Thr Gln
    2450                2455                2460

Phe Glu Glu Thr Trp Ala Thr Leu Leu Gly Val Leu Val Thr Gln
    2465                2470                2475

Pro Leu Val Met Glu Gln Glu Glu Ser Pro Pro Glu Glu Asp Thr
    2480                2485                2490

Glu Arg Thr Gln Ile Asn Val Leu Ala Val Gln Ala Ile Thr Ser
    2495                2500                2505

Leu Val Leu Ser Ala Met Thr Val Pro Val Ala Gly Asn Pro Ala
    2510                2515                2520

Val Ser Cys Leu Glu Gln Gln Pro Arg Asn Lys Pro Leu Lys Ala
    2525                2530                2535

```
Leu Asp Thr Arg Phe Gly Arg Lys Leu Ser Ile Ile Arg Gly Ile
2540                2545                2550

Val Glu Gln Glu Ile Gln Ala Met Val Ser Lys Arg Glu Asn Ile
2555                2560                2565

Ala Thr His His Leu Tyr Gln Ala Trp Asp Pro Val Pro Ser Leu
2570                2575                2580

Ser Pro Ala Thr Thr Gly Ala Leu Ile Ser His Glu Lys Leu Leu
2585                2590                2595

Leu Gln Ile Asn Pro Glu Arg Glu Leu Gly Ser Met Ser Tyr Lys
2600                2605                2610

Leu Gly Gln Val Ser Ile His Ser Val Trp Leu Gly Asn Ser Ile
2615                2620                2625

Thr Pro Leu Arg Glu Glu Trp Asp Glu Glu Glu Glu Glu
2630                2635                2640

Ala Asp Ala Pro Ala Pro Ser Ser Pro Thr Ser Pro Val Asn
2645                2650                2655

Ser Arg Lys His Arg Ala Gly Val Asp Ile His Ser Cys Ser Gln
2660                2665                2670

Phe Leu Leu Glu Leu Tyr Ser Arg Trp Ile Leu Pro Ser Ser Ser
2675                2680                2685

Ala Arg Arg Thr Pro Ala Ile Leu Ile Ser Glu Val Val Arg Ser
2690                2695                2700

Leu Leu Val Val Ser Asp Leu Phe Thr Glu Arg Asn Gln Phe Glu
2705                2710                2715

Leu Met Tyr Val Thr Leu Thr Glu Leu Arg Arg Val His Pro Ser
2720                2725                2730

Glu Asp Glu Ile Leu Ala Gln Tyr Leu Val Pro Ala Thr Cys Lys
2735                2740                2745

Ala Ala Ala Val Leu Gly Met Asp Lys Ala Val Ala Glu Pro Val
2750                2755                2760

Ser Arg Leu Leu Glu Ser Thr Leu Arg Ser Ser His Leu Pro Ser
2765                2770                2775

Arg Val Gly Ala Leu His Gly Val Leu Tyr Val Leu Glu Cys Asp
2780                2785                2790

Leu Leu Asp Asp Thr Ala Lys Gln Leu Ile Pro Val Ile Ser Asp
2795                2800                2805

Tyr Leu Leu Ser Asn Leu Lys Gly Ile Ala His Cys Val Asn Ile
2810                2815                2820

His Ser Gln Gln His Val Leu Val Met Cys Ala Thr Ala Phe Tyr
2825                2830                2835

Leu Ile Glu Asn Tyr Pro Leu Asp Val Gly Pro Glu Phe Ser Ala
2840                2845                2850

Ser Ile Ile Gln Met Cys Gly Val Met Leu Ser Gly Ser Glu Glu
2855                2860                2865

Ser Thr Pro Ser Ile Ile Tyr His Cys Ala Leu Arg Gly Leu Glu
2870                2875                2880

Arg Leu Leu Leu Ser Glu Gln Leu Ser Arg Leu Asp Ala Glu Ser
2885                2890                2895

Leu Val Lys Leu Ser Val Asp Arg Val Asn Val His Ser Pro His
2900                2905                2910

Arg Ala Met Ala Ala Leu Gly Leu Met Leu Thr Cys Met Tyr Thr
2915                2920                2925

Gly Lys Glu Lys Val Ser Pro Gly Arg Thr Ser Asp Pro Asn Pro
2930                2935                2940
```

-continued

```
Ala Ala Pro Asp Ser Glu Ser Val Ile Val Ala Met Glu Arg Val
    2945            2950                2955
Ser Val Leu Phe Asp Arg Ile Arg Lys Gly Phe Pro Cys Glu Ala
    2960            2965                2970
Arg Val Val Ala Arg Ile Leu Pro Gln Phe Leu Asp Asp Phe Phe
    2975            2980                2985
Pro Pro Gln Asp Ile Met Asn Lys Val Ile Gly Glu Phe Leu Ser
    2990            2995                3000
Asn Gln Gln Pro Tyr Pro Gln Phe Met Ala Thr Val Val Tyr Lys
    3005            3010                3015
Val Phe Gln Thr Leu His Ser Thr Gly Gln Ser Ser Met Val Arg
    3020            3025                3030
Asp Trp Val Met Leu Ser Leu Ser Asn Phe Thr Gln Arg Ala Pro
    3035            3040                3045
Val Ala Met Ala Thr Trp Ser Leu Ser Cys Phe Phe Val Ser Ala
    3050            3055                3060
Ser Thr Ser Pro Trp Val Ala Ala Ile Leu Pro His Val Ile Ser
    3065            3070                3075
Arg Met Gly Lys Leu Glu Gln Val Asp Val Asn Leu Phe Cys Leu
    3080            3085                3090
Val Ala Thr Asp Phe Tyr Arg His Gln Ile Glu Glu Glu Leu Asp
    3095            3100                3105
Arg Arg Ala Phe Gln Ser Val Leu Glu Val Val Ala Ala Pro Gly
    3110            3115                3120
Ser Pro Tyr His Arg Leu Leu Thr Cys Leu Arg Asn Val His Lys
    3125            3130                3135
Val Thr Thr Cys
    3140
```